(12) United States Patent
Bonutti

(10) Patent No.: US 6,592,609 B1
(45) Date of Patent: Jul. 15, 2003

(54) METHOD AND APPARATUS FOR SECURING TISSUE

(75) Inventor: Peter M. Bonutti, Effingham, IL (US)

(73) Assignee: Bonutti 2003 Trust-A, Effingham, IL (US)

( * ) Notice: Subject to any disclaimer, the term of this patent is extended or adjusted under 35 U.S.C. 154(b) by 0 days.

(21) Appl. No.: 09/556,458

(22) Filed: May 3, 2000

Related U.S. Application Data

(63) Continuation-in-part of application No. 09/524,397, filed on Mar. 13, 2000, now Pat. No. 6,368,343, and a continuation-in-part of application No. 09/523,442, filed on Mar. 10, 2000, now Pat. No. 6,475,230, and a continuation-in-part of application No. 09/370,865, filed on Aug. 9, 1999, now Pat. No. 6,447,516.

(51) Int. Cl.[7] .............................................. A61B 17/04

(52) U.S. Cl. ................................................... 606/232

(58) Field of Search .............................. 606/232, 139

(56) References Cited

U.S. PATENT DOCUMENTS

| | | | |
|---|---|---|---|
| 3,513,848 A | 5/1970 | Winston et al. ............. | 606/232 |
| 3,657,056 A | 4/1972 | Winston et al. ............. | 606/232 |
| 4,662,068 A | 5/1987 | Polonsky ..................... | 606/232 |
| 5,527,343 A | 6/1996 | Bonutti ....................... | 606/232 |
| 5,534,012 A | 7/1996 | Bonutti ....................... | 606/232 |
| 5,626,612 A | 5/1997 | Bartlett ....................... | 606/232 |
| 5,718,717 A * | 2/1998 | Bonutti ....................... | 606/139 |
| 5,823,994 A | 10/1998 | Sharkey et al. ............. | 606/232 |
| 5,928,267 A | 7/1999 | Bonutti et al. .............. | 606/232 |
| 5,948,002 A | 9/1999 | Bonutti ....................... | 606/232 |
| 5,964,765 A | 10/1999 | Fenton, Jr. et al. ......... | 606/232 |
| 5,968,047 A | 10/1999 | Reed ............................ | 606/232 |
| 5,989,282 A | 11/1999 | Bonutti ....................... | 606/232 |
| 5,993,477 A | 11/1999 | Vaitekunas et al. ......... | 606/232 |
| 6,010,525 A | 1/2000 | Bonutti et al. .............. | 606/232 |

OTHER PUBLICATIONS

Article entitled "The Search for the; Holy Grail: a Century of Anterior Cruciate Ligament Reconstruction", R. John Naranja, Jr., MD, Jeffrey R. Kuhlman, MD, and Joseph S. Torg, MD, Published by the American Journal of Orthopaedics, Nov. 1997, pp. 743–752.

Article under the heading Technical Note, entitled "Femoral Bone Plug Recession in Endoscopic Anterior Cruciate Ligament Reconstruction", By David E. Taylor, M.D., F.R.A.C.S., Gregory C. R. Keene, M.D., F.R.A.C.S., published by Arthroscopy: The Journal of Arthroscopic and Related Surgery, vol. 12, No. 4 (Aug.), 1996: 513–515.

Article under heading the Technical Note, entitled "Meniscus Replacement with Bone Anchors: A Surgical Technique", by Walter R. Shelton, M.D. and Andrea D. Dukes, B.S., published by Arthroscopy: The Journal of Arthroscopic and Related Surgery, vol. 10, No. 3, 1994, pp. 324–327.

* cited by examiner

Primary Examiner—Gary Jackson
(74) Attorney, Agent, or Firm—Fleit, Kain, Gibbons, Gutman & Bongini P.L.; Paul D. Bianco; Martin Fleit

(57) ABSTRACT

An anchor has a pointed end portion may be utilized to form an opening in a bone in a patient's body. The anchor is moved into the opening formed in the bone in the patient's body with a suture connected to the anchor. The suture may then be utilized to retain body tissue in a desired position relative to the bone. The body tissue may be either hard or soft body tissue. If desired the anchor may be utilized in conjunction with layers of soft body tissue. When a suture is used it may be secured by connecting a retainer with the suture. Alternatively, sections of the suture may be interconnected. It is believed that it may be preferred to secure the suture in place after at least a predetermined tension has been established in the suture and/or a predetermined force has been transmitted to the body tissue. The suture may be secured in place by exposing a retainer to ultrasonic vibratory energy or by applying the ultrasonic vibratory energy directly to sections of the suture.

162 Claims, 7 Drawing Sheets

METHOD AND APPARATUS FOR SECURING TISSUE

RELATED APPLICATIONS

This application is a continuation-in-part of U.S. patent application Ser. No. 09/524,397 filed Mar. 13, 2000 now U.S. Pat. No. 6,368,343 by Peter M. Bonutti et al. and entitled "Method of Using Ultrasonic Vibration to Secure Body Tissue". This application is also a continuation-in-part of U.S. patent application Ser. No. 09/523,442 filed Mar. 10, 2000 now U.S. Pat. No. 6,475,230 by Peter M. Bonutti et al. and entitled "Method and Apparatus for Securing a Suture". This application is also a continuation-in-part of application Ser. No. 09/370,865 filed Aug. 9, 1999 now U.S. Pat. No. 6,447,516 by Peter M. Bonutti and entitled "Method of Securing Tissue". The benefit of the earlier filing dates of the aforementioned applications is hereby claimed for all subject matter common to this application and any one of the aforementioned applications. The disclosures in the aforementioned applications are hereby incorporated herein in their entirety by this reference thereto.

BACKGROUND OF THE INVENTION

The present invention relates to a new and improved method and apparatus for securing tissue in a patient's body. The method and apparatus may be utilized to secure hard tissue and/or soft tissue in a patient's body.

Anchors have previously been utilized to retain sutures in a patient's body. The anchors have previously been formed of metal, such as stainless steel or titanium. In addition, anchors have been formed of biodegradable materials. Anchors have also been formed of bone. It has previously been suggested to construct anchors in the manner disclosed in U.S. Pat. Nos. 5,527,343; 5,534,012; 5,928,267; and 5,989,282. The disclosures in the aforementioned patents are hereby incorporated herein in their entirety by this reference thereto.

It has previously been suggested that ultrasonic vibratory energy be utilized to interconnect sections of a suture in the manner disclosed in U.S. Pat. No. 3,513,848. This patent suggests that the suture is initially tensioned by a surgeon or his assistant by gripping free ends of the suture and applying the requisite force. While the requisite force is maintained, ultrasonic energy is applied to the segments of the suture. The high frequency mechanical vibrations applied to the suture result in bonding of overlapping areas on segments of the suture. It has also been suggested that ultrasonic energy could be utilized in connecting an elongated element with a fusible receptacle in the manner disclosed in U.S. Pat. No. 5,964,765.

When tissue is to be secured against movement relative to a portion of a bone, it is necessary to interconnect the bone and the tissue. In this situation, it has been a common practice to drill a hole which extends into or through the bone. A retaining member, such as a pin, screw or suture anchor is positioned in the hole after it has been drilled in the bone. The concept of utilizing a retainer member formed of bone to anchor a suture is disclosed in U.S. Pat. No. 5,626,612. It has also been suggested that screws, pins, anchors and plates could be fabricated from bone in the manner disclosed in U.S. Pat. No. 5,968,047.

SUMMARY OF THE INVENTION

The present invention relates to a method and apparatus for use in securing soft tissue, hard tissue, or hard and soft tissue in a patient's body. The hard tissue may be any one of the many bones in a patient's body. The soft tissue may be any one of the tissues in a patient's body other than the hard tissue.

The tissue may be secured by using a suture. The suture may be connected with an anchor. When an anchor is utilized in association with a suture, the anchor may be formed of any one of many different materials including bone or other body tissue, biodegradable materials, or non-biodegradable materials. The anchor may be formed of two or more different materials.

When a suture is utilized to secure body tissue, a retainer may be connected with the suture. Alternatively, sections of the suture may be connected with each other.

If a suture is utilized to secure body tissue, an apparatus may advantageously be provided to tension the suture with a predetermined force. If a retainer is utilized in association with the suture, the apparatus may urge the retainer toward the body tissue with a predetermined force. The retainer may be connected with the suture in response to detection of at least a predetermined tension in the suture and/or the transmission of a predetermined force to the body tissue. When the retainer is to be eliminated, sections of the suture may be interconnected in response to detection of a predetermined tension in the suture and/or detection of the transmission of a predetermined force to the body tissue.

The anchor, for some uses at least, may be formed of a single piece of bone. A pointed end portion of the anchor may have a surface which forms an opening in a bone or other tissue in a patient's body. The anchor may be moved into the opening formed in the tissue by the pointed leading end portion of the anchor.

It should be understood that in certain situations, it may be desired to use just a suture, without an anchor, to secure the body tissue. In these situations, a retainer may be connected with the suture. Alternatively, sections of the suture may be directly connected with each other. In other situations, it may be desired to use an anchor, without a suture, to secure body tissue.

BRIEF DESCRIPTION OF THE DRAWINGS

The foregoing and other features of the present invention will become more apparent upon a consideration of the following description taken in connection with the accompanying drawings wherein.

DESCRIPTION OF SPECIFIC PREFERRED EMBODIMENTS OF THE INVENTION

Anchor

Figure 1:
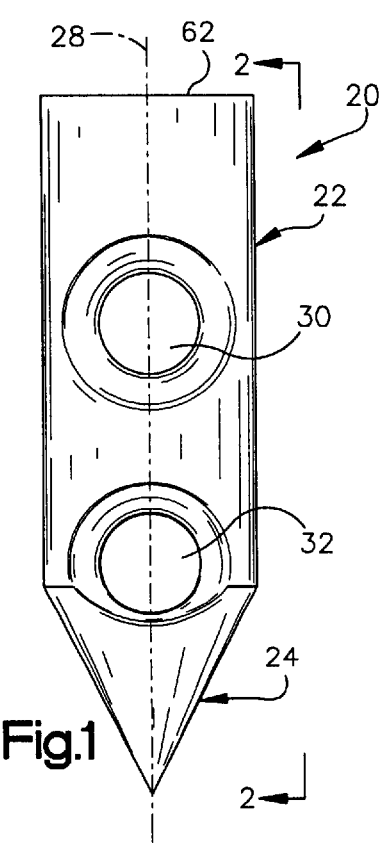
FIG. 1 is an enlarged plan view of an anchor which may be utilized in securing body tissue.
Figure 2:
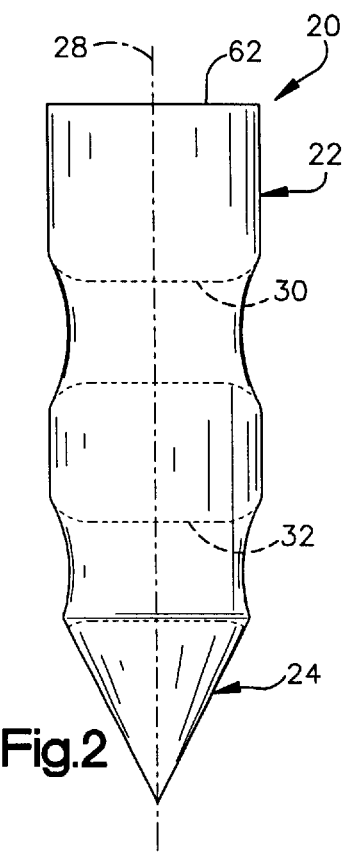
FIG. 2 is a side elevational view, taken generally along the line 2—2 of FIG. 1, further illustrating the construction of the anchor.

One specific anchor 20 constructed in accordance with the present invention is illustrated in FIGS. 1 and 2. The anchor 20 may be utilized to secure a suture relative to body tissue in a patient's body. However, it is contemplated that, in some situations at least, the anchor 20 may be utilized without a suture.

The anchor 20 is formed of a single piece of bone, specifically, hard compact bone (cortical bone). The bone from which the anchor 20 is formed may be autogenic bone or allogenic bone. Alternatively, the anchor 20 may be formed of xenogenic bone.

Although the anchor 20 may be formed of bone obtained from many different sources, it is believed that it may be preferred to form the anchor 20 of freeze dried bone which has been obtained from a human cadaver. The bone may be harvested under clean conditions and treated to achieve sterility. Of course, the bone forming the anchor 20 could be obtained in any one of many different manners under any one of many different conditions.

Although it is preferred to form the anchor 20 of bone, the anchor may be formed of other materials if desired. The anchor 20 may be formed of biodegradable or nonbiodegradable materials. For example, the anchor 20 may be formed of polycaperlactone. The anchor 20 may be formed of metal, such as titanium or stainless steel. Alternatively, the anchor 20 may be formed of biodegradable or bioerodible copolymers.

The anchor 20 is formed of a single piece of bone and includes a cylindrical body portion 22 and a pointed end portion 24. The pointed end portion 24 has a conical configuration. The cylindrical body portion 22 and pointed end portion 24 have a common longitudinal central axis 28 which extends axially through the anchor 20.

Although the pointed end portion 24 has a conical configuration, the pointed end portion could have a different configuration if desired. For example, the pointed end portion could be wedge-shaped. Alternatively, the pointed end portion 24 could have a pyramidal configuration and be formed by the intersection of three, four, or more surfaces. The surfaces could be flat or concave in configuration.

It is contemplated that the anchor 20 may be used in association with a suture. If and when the anchor 20 is to be used with a suture, the anchor is provided with a pair of passages 30 and 32. The passages 30 and 32 have a cylindrical configuration and extend diametrically through the cylindrical body portion 22. Central axes of the passages 30 and 32 extend parallel to each other and intersect the central axis 28 of the anchor 20.

The passage 30 is formed entirely in the body section 22. However, the passage 32 is formed partially in the body section 22 and partially in the pointed end portion 34. Thus, the major portion of the passage 32 is formed in the body portion 22. However, a minor portion of the passage 32 extends into the pointed end portion 24.

In the illustrated embodiment of the anchor 20, two passages 30 and 32 extend diametrically through the cylindrical body portion 22 of the anchor. However, it is contemplated that only a single passage may be provided through the anchor. This single passage could be skewed at an acute angle relative to the central axis 28 of the anchor 20. Alternatively, the passage could extend axially through the anchor.

Although it is preferred to provide the anchor 20 with the pointed leading end portion 24, it is contemplated that the anchor 20 could have a different configuration. For example, the anchor 20 could have the configuration of any one of the anchors illustrated in U.S. Pat. No. 5,527,343 or U.S. Pat. No. 5,534,012. The disclosures in the aforementioned U.S. Pat. Nos. 5,534,012 and 5,527,343 have been and hereby are incorporated herein in their entirety.

In one specific embodiment of the anchor 20, intended for use with a suture, the anchor had an overall length of approximately 0.236 inches and a body portion 22 with a diameter of approximately 0.072 inches. The passages 30 and 32 had diameters of approximately 0.035 inches. Another embodiment of the anchor 20 had an overall length of approximately 0.354 inches and a body portion 22 with a diameter of approximately 0.119 inches. The passages 30 and 32 in the specific anchor had a diameter of approximately 0.046 inches.

It should be understood that the foregoing dimensions of specific embodiments of the anchor 20 have been set forth herein for purposes of clarity of description. It is contemplated that the anchor 20 will be formed with dimensions which are different than these specific dimensions. For example, an anchor 20 intended for use without a suture may have a length which is different than the specific lengths previously set forth herein. Similarly, anchors intended for use with soft body tissue may have dimensions which are different than dimensions of anchors intended for use with hard body tissue.

The specific embodiment of the anchor 20 described herein is formed of bone. Specifically, the anchor 20 is formed of a single piece of human bone. However, the anchor 20 may be formed of other materials if desired. For example, the anchor 20 may be formed of titanium or titanium alloys. Alternatively, the anchor 20 may be formed of stainless steel. The anchor 20 may be formed of any one of many known biodegradable materials. The anchor 20 may be formed of either biodegradable or nonbiodegradable polymeric materials.

Positioning of Anchor Relative to Body Tissue

The anchor 20 of FIGS. 1 and 2 may be utilized to secure a suture 36 (FIG. 3) relative to body tissue. The suture 36 may be formed of a plastic material which is a biopolymer. In one specific embodiment of the invention, the suture 36 is formed of polyglycolide which is commercially available under the trademark DEXON. Polyglycolide is a crystalline material that melts at about 225° Celsius. Although the suture 36 is a monofilament suture having a continuous cylindrical outer side surface, it is contemplated that the suture could be formed in a different manner. For example, the suture 36 could be a cable having an interlaced structure formed by a plurality of filaments or strands which have been twisted, braided, twined, and/or threaded together.

It is also contemplated that the suture 36 may be formed of a polyglycolide-based copolymer, specifically, 10/90 P-LL/G (10% poly I-lactide and 90% glycolide) which is commercially available under the trademark VICRYL, VICRYL is a crystalline material that melts at about 205° Celsius. VICRYL can be used for either a monofilament or a braided suture. The suture 36 may have a construction which is similar to the construction of the sutures disclosed in U.S. Pat. No. 5,928,267. The aforementioned U.S. Pat. No. 5,928,267 has been and hereby is incorporated herein in its entirety.

The strength of the suture 36 will vary as a function of the size of the suture. It is contemplated that the specific strength of a particular suture size will vary depending upon the material from which the suture is constructed and the manufacturer of the suture. By consulting a chart, a surgeon can select a suture of a size and strength suitable for a particular use. Thus, a relatively large suture having substantial strength may be selected when body tissue is to be connected with a bone or when portions of a bone are to be interconnected by the suture. On the other hand, a relatively small suture size having a relatively small strength may be selected when delicate body tissue, such as stomach or intestinal tissue is to be interconnected with the suture.

The manner in which the suture size and strength varies is explained in the aforementioned U.S. patent application Ser. No. 09/523,422, filed Mar. 10, 2000 and entitled "Method and Apparatus for Securing a Suture". The disclosure in the aforementioned U.S. patent application Ser. No. 09/523,422 has been and hereby is incorporated herein in its entirety.

Figure 3:
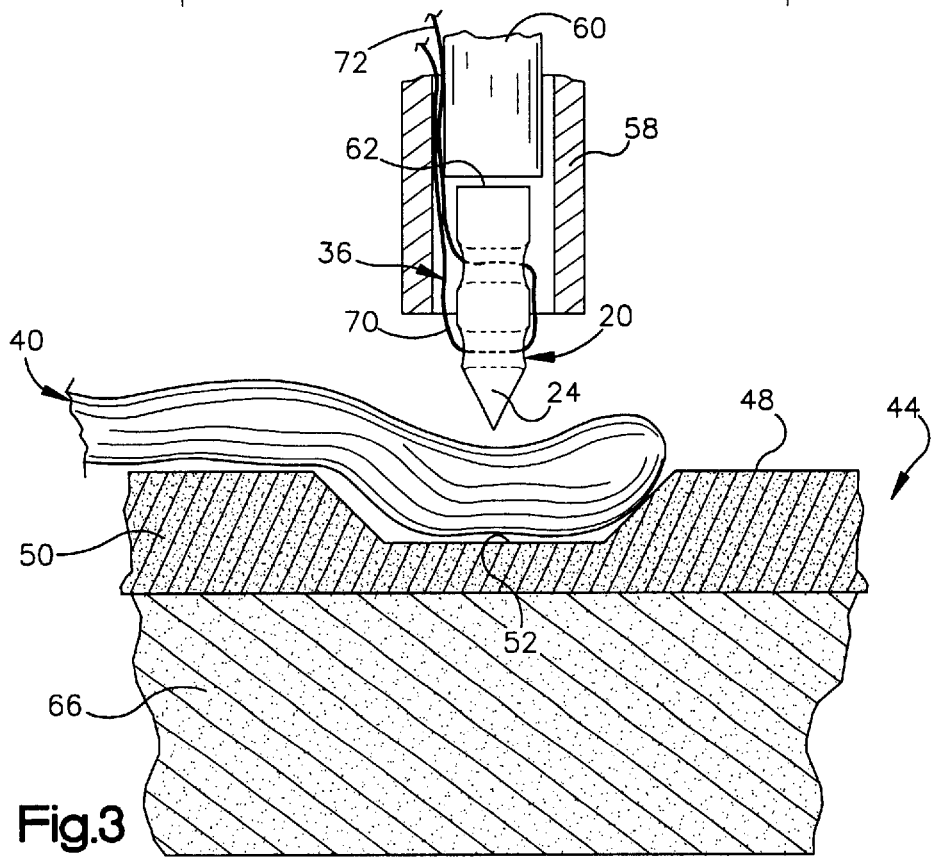
FIG. 3 is a fragmentary schematic illustration depicting, on a reduced scale, one of the ways in which the anchor of FIGS. 1 and 2 may be positioned relative to hard and soft body tissue.

In the embodiment of the invention illustrated in FIG. 3, the anchor 20 is utilized with a suture 36. The specific anchor 20 illustrated in FIG. 3 is integrally formed as one piece of freeze dried human bone. The anchor 20 and suture 30 are utilized to hold soft body tissue 40 against movement relative to a portion of a bone 44 in a human patient's body. The tissue 40 is connective tissue, such as a ligament or tendon. However, the tissue 40 could be other types of tissue if desired.

When the tissue 40 is to be connected with the bone 44, the anchor 20 is utilized to initiate the formation of an opening in the bone at a location which is free of naturally occurring openings. Prior to formation of an opening in the bone 44 with the anchor 20, a hard outer surface 48 is removed from a compact outer layer 50 of bone by a decortation process. The decortation process is performed by abrading the hard outer surface 48 on the compact outer layer 50 of hard cortical bone to expose an imperforate inner area 52 at a location where the anchor 20 and suture 36 are to be utilized to connect the body tissue 40 with the bone 44. Once the decortation process has been completed, the soft body tissue 40 is positioned in engagement with the inner area 52 in the manner illustrated schematically in FIG. 3. The decortation process is optional and may be omitted if desired.

The anchor 20 is then moved through the body tissue 40 into the bone 44. It is believed that it will be preferred to move the anchor 20 into the bone 44 under the influence of an axial force applied against a trailing end portion of the anchor. Since the bone forming the anchor 20 has a relatively high compressive strength, the anchor can be utilized to transmit relatively large forces along the longitudinal central axis 28 (FIG. 1) of the anchor to force the anchor into the bone 44. However, bone has a relatively low tensile strength and can not transmit large transverse loads. Therefore, when the anchor 20 is moved into the bone 44 under the influence of axial force applied against a trailing end of the anchor, there may be a tendency for the anchor to shear or fail by a lateral buckling or fracture of the anchor rather than by direct compression of the anchor.

In order to support the anchor 20 during movement of the anchor into the bone 44, the anchor is advantageously inserted into a tubular cylindrical metal sleeve or member 58 (FIG. 3). A cylindrical pusher member 60 is received in the cylindrical sleeve 58 and is utilized to apply an axial force to a circular trailing end surface 62 on the anchor 20. Although the sleeve and pusher member 58 and 60 could have many different configurations and cooperate with each other in many different manners, it may be preferred to utilize a sleeve 58 and pusher member 60 having a construction similar to the construction illustrated in U.S. Pat. No. 5,948,002. The disclosure in the aforementioned U.S. Pat. No. 5,948,002 is hereby incorporated herein in its entirety by this reference thereto. Of course, different types of devices could be utilized to move the anchor 20 into the body tissue 40 and bone 44 if desired.

When the anchor is to be moved through the body tissue 40 into the bone 44, the pointed end portion 24 of the anchor is aligned with the body tissue 40 at a location where the anchor is to be moved into the body tissue. The sleeve 58 is then pressed firmly against the body tissue 40. Although a substantial space has been shown between the inner surface of the sleeve 58 and the cylindrical outer side surface of the anchor 20 in FIG. 3 for purposes of clarity of illustration, it is contemplated that there will be a relatively snug fit of the anchor 20 and pusher member 60 with the inner side surface of the sleeve 58. However, the anchor 20 and pusher member 60 will be freely movable in an axial direction along the sleeve 58.

The pusher member 60 is then pressed firmly against the trailing surface 62 on the anchor 20. This force easily moves the pointed leading end portion 24 of the anchor 20 through the soft body tissue 40 into engagement with an imperforate surface area on the compact outer layer 50 of the bone 44.

The anchor 20 is moved out of the tubular sleeve 58 into the compact outer layer 50 of the bone 44 at a location which is free of naturally occurring openings (FIG. 3). To move the anchor 20 out of the sleeve 58 into the bone 44, the pusher member applies an axial force against the trailing end surface 62 on the anchor 20. The axial force applied by the pusher member 60 moves the pointed leading end portion 24 of the anchor into the compact outer layer 50 of bone. The tubular sleeve 58 engages the cylindrical outer side surface of the anchor 20 to support the anchor against sidewise loading. This results in the anchor being subjected primarily to compressive force as the anchor is moved into the bone 44.

As the anchor 20 moves into the bone 44, the material of the compact outer layer 50 of the bone is displaced sideways by the leading end portion 24 of the anchor 20. As the anchor 20 continues to move into the compact outer layer 50 of the bone 44, the material of the compact outer layer supports the anchor against transverse loading in much the same manner in which the tubular sleeve 58 supports the anchor. Therefore, the pusher member 60 can apply relatively large axial force to the anchor 20 without failure, that is, without fracture or buckling of the anchor.

The anchor 20 is utilized to initiate formation of an opening in the compact outer layer 50 of the bone 44 at a location which is free of openings. However, if desired, a relatively small pilot opening could be drilled through the compact outer layer 50 of the bone 44. The anchor 20 would then be utilized to form the small pilot opening into a larger opening through which the anchor can pass.

The anchor 20 is moved through a desired distance into the bone 44. In order to facilitate determination of when the anchor 20 is moved through the desired distance into the bone 44, indicia may be provided on the pusher member 20. The indicia on the pusher member 60 cooperates with the sleeve 58 to indicate when the anchor 20 has moved through a desired distance into the bone 44. The application of force against the anchor 20 by the pusher member 36 is then interrupted. The manner in which the sleeve 58 and pusher member 60 cooperate with the anchor 20 is the same as disclosed in U.S. patent application Ser. No. 09/370,865 filed Aug. 9, 1999 by Peter M. Bonutti and entitled "Method of Securing Tissue". The disclosure in the aforementioned U.S. patent application Ser. No. 09/370,865 has been and hereby is incorporated herein in its entirety.

It is contemplated that the anchor 20 may be utilized, without the suture 36, to connect the body tissue 40 with the bone 44. When the anchor 20 is to be used in this manner, the anchor 20 will engage both the body tissue 40 and the bone 44. However, the illustrated embodiment of the anchor 20 is intended for use with the suture 36.

The pusher member 60 is effective to push the anchor 20 through the compact outer layer 50 of hard cortical bone into relatively soft cancellous bone 66 which is enclosed by the hard compact outer layer 50. As the pointed leading end portion 24 of the anchor 20 enters the cancellous bone 66, the pointed end portion pushes the cancellous bone 66 aside to form an opening in the cancellous bone. The anchor moves into the cancellous bone 66 along a straight path having a longitudinal axis which is coincident with a longitudinal central axis of the sleeve 58. Therefore, the pointed end portion 24 of the anchor is effective to push aside tissue forming the compact outer layer 50 and the cancellous bone 66 as the anchor moves into the bone 44.

Figure 4:
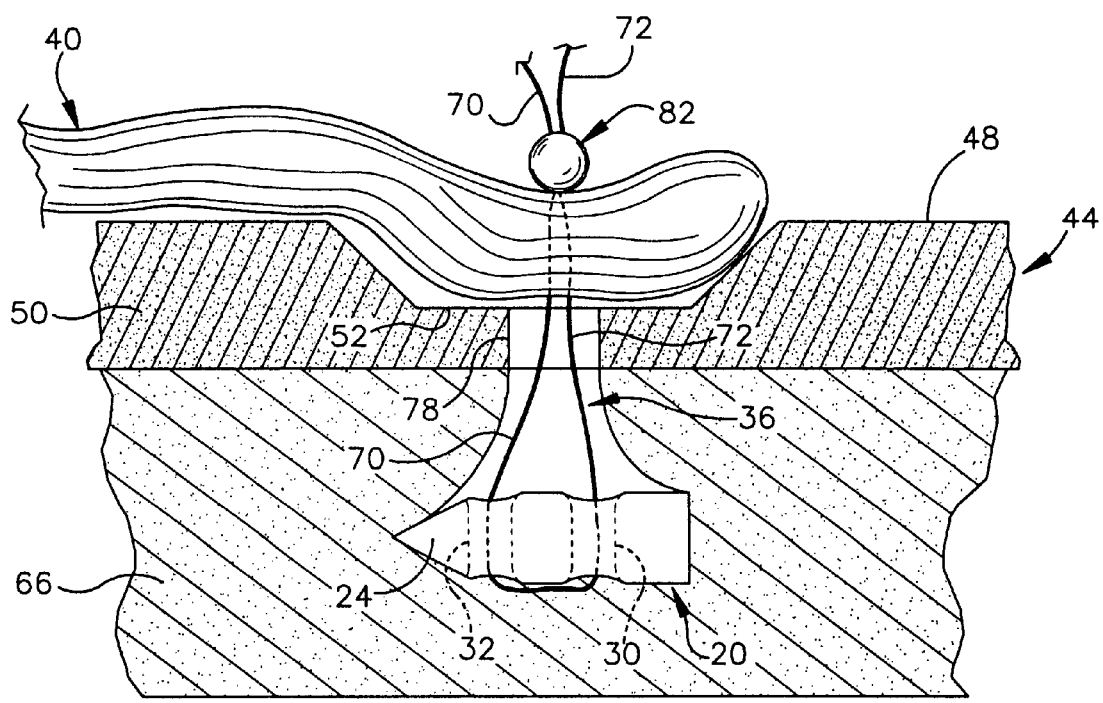
FIG. 4 is a schematic fragmentary illustration depicting one way in which the anchor of FIG. 3 may connected with body tissue utilizing a retainer connected with a suture.

When the anchor has moved through a predetermined distance into the cancellous bone 66, the anchor is pivoted from the orientation illustrated in FIG. 3 to the orientation illustrated in FIG. 4. Thus, after the end surface 62 on the anchor 20 has moved past the inner side surface of the compact outer layer 50 and into the cancellous bone 66, the orientation of the anchor 20 relative to the bone 44 is changed by rotating the anchor through ninety degrees (90°) with a toggling action.

To initiate the toggling action, a section 70 of the suture 36 extending through the anchor passage 32 to a location outside of the bone is tensioned. At this time, a second section 72, which extends through the anchor passage 30, is relaxed. There is enough friction between the section 70 of the suture and the freeze-dried bone forming the anchor 20 to initiate a pivoting action of the anchor.

Once this pivoting action has been initiated, the pusher member 60 (FIG. 3) is pressed against a circular rim on the end surface 62 and the tension in the section 70 of the suture is increased. As the tension in the section 70 of the suture is increased, the suture tends to slide relative to the material forming the anchor 20. Therefore, the tension in the section 72 of the suture 36 is increased. However, the tension in the section 70 of the suture will tend to be larger than the tension in the section 72 of the suture.

Once the anchor 20 begins to rotate with a toggling action, the pusher member 60 is pressed against the rim of the end surface 62 to maintain the anchor at the desired depth in the cancellous bone 66. At the same time, the tension in the sections 70 and 72 of the suture 36 applies torque to the anchor to rotate the anchor about the location where the anchor engages the pusher member 60. The anchor 20 rotates with a toggling action in the manner disclosed in the aforementioned U.S. Pat. Nos. 5,527,343; 5,534,012; and 5,948,002. The aforementioned patents have been and hereby are incorporated herein in their entirety.

Once the anchor 20 has pivoted to the orientation illustrated in FIG. 4, the sections 70 and 72 of the suture 36 can be freely moved in the passages 32 and 30 extending through the anchor. This enables the sections 70 and 72 of the suture 36 to be moved relative to each other so that they have the desired length.

The anchor 20 is supported in the cancellous bone 66 in a spaced-apart relationship with the compact outer layer 50 of bone. The anchor 20 is entirely surrounded by a matrix of the cancellous bone 66. The anchor 20 does not touch the compact outer layer 50 of bone. Tension forces applied to the anchor 20 by the suture 36 are transmitted from the outer side surface of the anchor to the cancellous bone to hold the anchor against movement relative to the bone 44.

The suture 36 extends through an opening 78 in the compact outer layer 50 of bone into the soft body tissue 40. The suture extends through the soft body tissue to a location disposed on a side of the soft body tissue opposite from the bone 44. The suture 36 extends through the body tissue 40 along the same path which the anchor was moved through the body tissue 40 from the position shown in FIG. 3 to the position shown in FIG. 4. The viscoelastic nature of the soft body tissue 40 results in closing of the opening formed in the body tissue 40 by passage of the anchor 20 through the body tissue. However, the sections 70 and 72 of the suture remain in the closed passage through the body tissue 40 along which the anchor 20 previously moved.

The suture 36 may be connected with the soft body tissue in any one of many different ways. In the embodiment of the invention illustrated in FIG. 4, a retainer 82 is connected with the sections 70 and 72 of the suture 36. Although the sections 70 and 72 of the suture 36 could extend straight through the retainer 82, it is preferred to form a plurality of bends in the suture by wrapping the suture around a portion of the retainer.

The illustrated retainer 82 has a spherical configuration with a cylindrical passage which extends diametrically through the center of the retainer. The sections 70 and 72 of the suture 36 may be wrapped around the retainer 82 and passed through the passage through the retainer a plurality of times. Thus, the section 70 of the suture 36 extends through the passage in the retainer 82, around the outer side surface of the retainer and back through the passage again. The section 72 of the suture 36 also extends through the passage in the retainer 82, around the outside of the retainer and back through the passage in the retainer. If desired, the retainer 82 could have a different configuration and the suture 36 could be connected with the retainer in a different manner if desired.

After the suture 36 has been inserted through the retainer 82, the retainer 82 is moved along the sections 70 and 72 of the suture toward the body tissue 40. As the retainer 82 is moved along the sections 70 and 72 of the suture 36 toward the body tissue 40, the retainer moves into engagement with the body tissue. The sections 70 and 72 of the suture 36 are then tensioned with a predetermined force. This predetermined tension force is transmitted through the retainer 82 to the anchor 20. At the same time, the retainer 82 is pressed downward against the body tissue 40 with a predetermined force.

This results in the soft body tissue 40 being compressed against the inner area 52 on the compact outer layer 50 of bone with a predetermined force while a predetermined tension force is transmitted through the suture 36 to the anchor 20. In this manner, a desired force, which has been preselected as a function of the size of the suture 36 and the characteristics of the soft body tissue 40 and bone 44 is applied against the body tissue and the bone by the anchor 20 and retainer 82. Although the retainer 82 applies force against a far greater surface area on the soft body tissue 40 than would be engaged by a knot in the suture 36, a force distribution member or button may be placed between the retainer 82 and the upper surface of the soft body tissue.

Once the retainer 82 has been moved along the suture 36 and is being pressed against the soft body tissue 40 with a predetermined force while a predetermined tension is maintained in the sections 70 and 72 of the suture 36, the suture retainer 82 is connected with the suture 36. The suture retainer 82 may be connected with the suture 36 in any one of many different ways. However, the retainer 82 is connected with the suture 36 by plastically deforming the retainer to effect a cold flowing of material of the retainer.

Force is applied against opposite sides of the retainer 82 by a pair of force application members with a clamping action. This force is effective to cause flowing of the material of the retainer 82 at a temperature below a transition temperature range for the material of the retainer. The cold flowing of the material of the retainer 82 results in a collapsing of the passage through the retainer and a flowing of the material of the retainer around the sections 70 and 72 of the suture. This enables the material of the retainer 82 to bond to and obtain a firm grip on the suture 36. The cold flowing of the material of the retainer 82 occurs at a temperature which is below the transition temperature of the material forming the retainer.

As the material of the retainer 82 is deformed, the material of the retainer bonds to the suture 36. When the suture 36 is of the cable type and formed by a plurality of interconnected filaments or strands, the material of the retainer 82 flows around and between the strands. The material of the retainer 82 flows completely around portions of each individual strand and bonds to each individual strand. In addition, the material of the retainer 82 flows around the intertwined suture strands and bonds to them as a group. Of course, if the suture 36 is a monofilament, the material of the retainer bonds to only the single strand or filament.

The retainer 82 may be formed of many different materials. However, it is believed that it will be preferred to form the retainer 82 of a biodegradable polymer. Once biodegradable polymer which may be utilized is polycaperlactone. Alternatively, the retainer 82 could be formed of polyethylene oxide terephthalate or polybutylene terephthalate. It is contemplated that other biodegradable or bioerodible copolymers could be utilized. It is believed that it will be preferred to form the suture 36 of the same material as the retainer 82. Thus, the suture 36 could be formed of any one of the materials previously suggested for forming the retainer 82.

It is preferred to effect the cold flowing of the material of the suture retainer 82 without the addition of heat. However, it is contemplated that the suture retainer 82 could be heated to a temperature which is somewhat above the temperature of the body tissue 40. If desired, heat could be transmitted to the retainer 82 through force application members which effect plastic deformation of the material of the retainer. When the suture 36 has a plurality of twisted strands, flowing of the material of the retainer 82 around the strands of the suture is promoted by heating of the retainer.

The construction of the retainer 82 and the manner in which it cooperates with the suture 36 is the same as is disclosed in the aforementioned U.S. patent application Ser. No. 09/523,442 filed Mar. 10, 2000 by Peter M. Bonutti et al. and entitled "Method and Apparatus for Securing a Suture". The disclosure in the aforementioned application Ser. No. 09/523,442 has been and hereby is incorporated herein in its entirety.

Although one specific retainer 82 has been described in connection with the embodiment of the invention illustrated in FIG. 4, it is contemplated that the retainer 82 could have a different construction if desired. For example, the retainer 82 could have any one of the constructions disclosed in the aforementioned application Ser. No. 09/523,442. Alternatively, the retainer 82 could have a different known construction.

Figure 5:
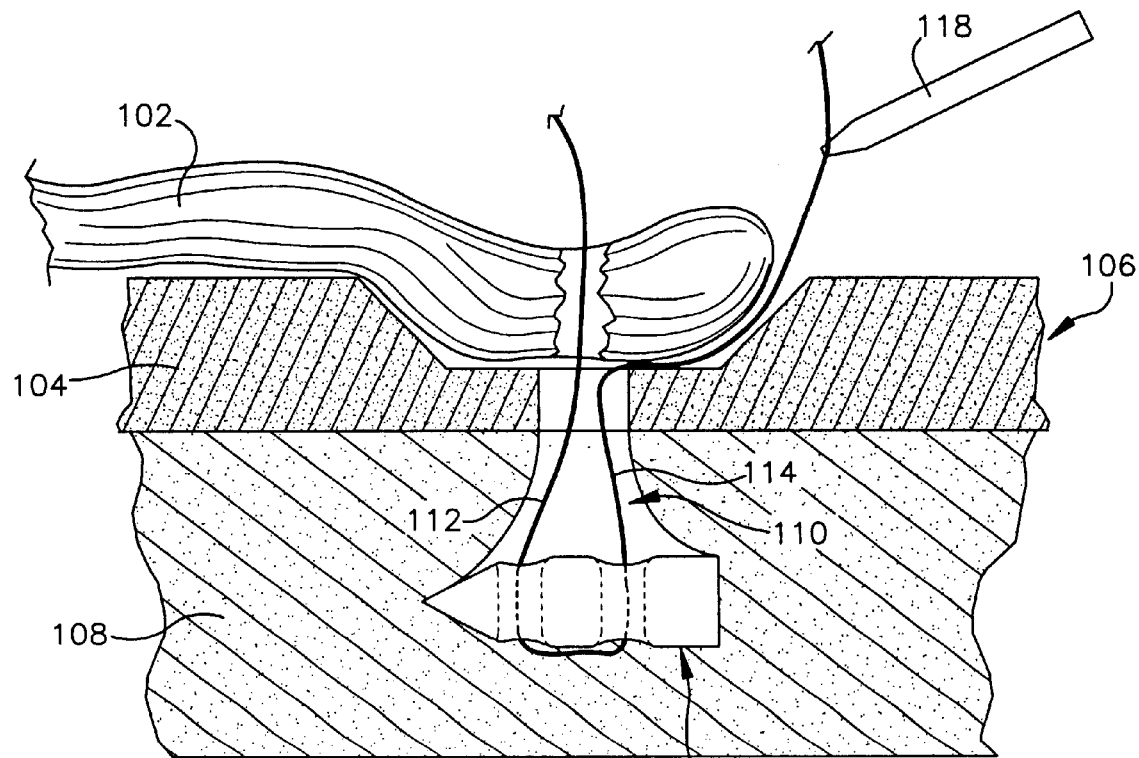
FIG. 5 is a fragmentary schematic sectional view, generally similar to FIG. 4, illustrating how one section of a suture is connected with an anchor embedded in cancellous bone and extends through soft tissue while another section of the suture is positioned to extend around the soft tissue.
Figure 6:
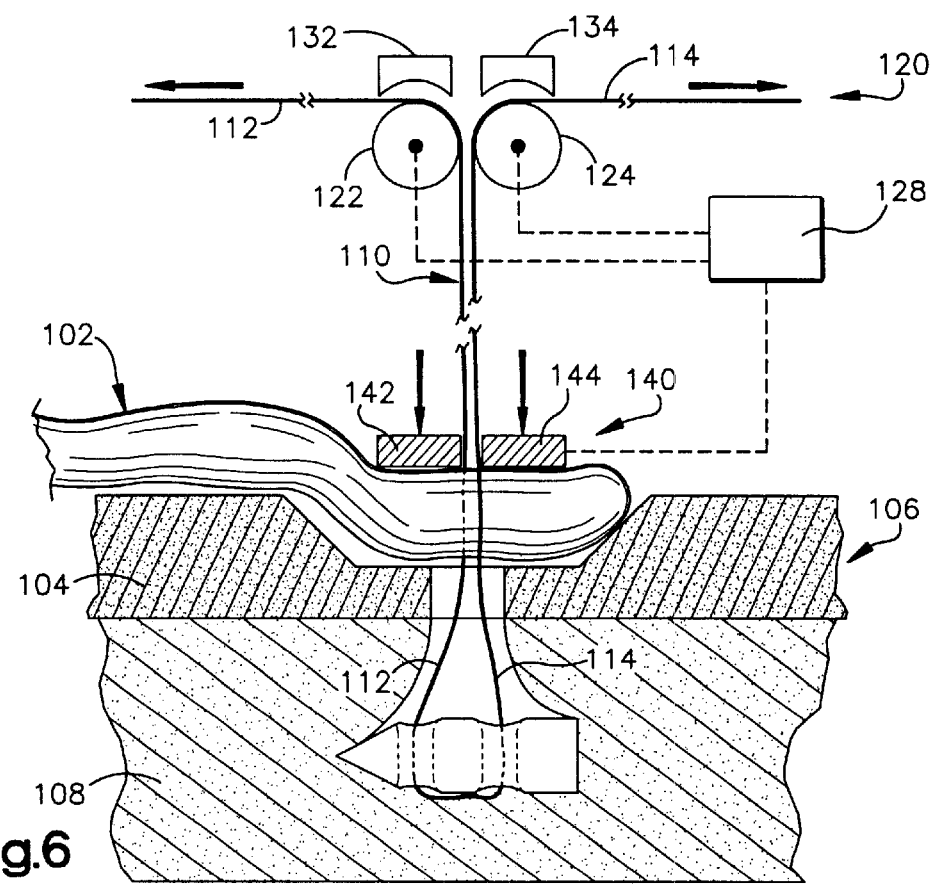
FIG. 6 is a fragmentary schematic illustration depicting the manner in which the suture of FIG. 5 is tensioned with a predetermined force and a connector assembly is utilized to press soft tissue against the bone prior to utilization of the assembly to interconnect sections of the suture.

Embodiment of FIGS. 5 and 6 In the embodiment of the invention illustrated in FIGS. 1–4, the sections 70 and 72 of the suture 36 extend through the body tissue 40 and are connected with a retainer 82. In the embodiment of the invention illustrated in FIGS. 5 and 6, one of the sections of the suture extends through the body tissue while the other section of the suture extends around the outside of the body tissue. In the embodiment of the invention illustrated in FIGS. 5 and 6, the retainer is eliminated and the sections of the suture are connected directly to each other. Since the embodiment of the invention illustrated in FIGS. 5 and 6 is similar to the embodiment of the invention illustrated in FIGS. 1–4, similar terminology will be utilized to identify similar components. It should be understood that one or more of the features of the embodiment of the invention illustrated in FIGS. 1–4 may be used with the embodiment of the invention illustrated in FIGS. 5 and 6.

An anchor 100 has the same construction as the anchor 20 of FIGS. 1 and 2. The specific anchor 100 of FIGS. 5 and 6 is integrally formed as one piece of freeze dried human bone. The anchor 100 is inserted through soft body tissue in the same manner as was previously described in conjunction with the embodiment of the invention illustrated in FIGS. 3 and 4. In addition, the anchor 100 was moved through a compact outer layer 104 of a bone 106 into cancellous bone 108 in the same manner as was previously described in connection with FIGS. 3 and 4. The anchor 100 is supported in the cancellous bone 108 in a spaced-apart relationship with the compact outer layer 104 of the bone 106.

A suture 110 extends through passages in the anchor 100. The suture 110 may have either a cable-like or a monofilament construction. The suture 110 may be a cable having strands formed of any of the materials mentioned in conjunction with the suture 36 of FIGS. 3 and 4. However, the illustrated suture 110 is a monofilament having a continuous cylindrical outer side surface.

Sections 112 and 114 of the suture 110 are pulled through the soft body tissue 102 and into the bone 106 as the anchor 100 is inserted into the bone in the manner previously explained in conjunction with the embodiment of the invention illustrated in FIG. 3. However, in the embodiment of the invention illustrated in FIGS. 5 and 6, it is desired to have one of the sections of the suture extend around the outside of the soft body tissue 102 while the other section of the suture extends through the body tissue. Thus, a gripper, illustrated schematically at 118 in FIG. 5, grips the section 114 of the suture 110 and pulls the section 114 of the suture out of the soft body tissue 102 after the anchor 100 has been positioned in the cancellous bone 108. Although the section 114 of the suture 110 is withdrawn from the soft body tissue 102, the section 112 of the suture remains extending through the soft body tissue in the manner illustrated schematically in FIG. 5. The section 114 of the suture 110 is wrapped around the outside of the body tissue and pulled into engagement with the section 112 of the suture.

Once the sections 112 and 114 of the suture 110 have been positioned relative to the body tissue 102, the sections 112 and 114 of the suture are tensioned with a predetermined force. At the same time, the soft body tissue 102 is pressed against the hard compact outer layer 104 of the bone 106 with a predetermined force. The two sections 112 and 114 of the suture 110 are then connected with each other to hold the soft body tissue 102 in a desired relationship with the bone 106. If desired, a force distribution member, such as a button, may be provided between the suture 110 and the soft body tissue 102.

An apparatus 120 for tensioning the two sections 112 and 114 of the suture 110 has been illustrated schematically in FIG. 6. The apparatus 120 includes a pair of rotatable wheels or pulleys 122 and 124. The rotatable wheels or pulleys 122 and 124 are connected to force measurement transducers which have an output which is proportional to the sideward force applied to the wheels. Thus, when the suture section 112 is tensioned, a leftward force (as viewed in FIG. 6) is applied to the rotatable wheel 122. A transducer connected with the wheel 122 is effective to provide an output signal which varies as a function of the leftward force applied to the wheel 122 by the suture 112. Of course, as the tension in the suture increases, the sideward force applied against the wheel 122 increases.

Although many different types of known force measuring transducers may be utilized, a solid state force measuring transducer may be preferred. The solid state force measuring device may be a piezoelectric transducer using a piezoelectric crystal as a sensitive unit. The output from the transducer is transmitted to a controller 128.

Similarly, the wheel 124 is connected with a force measuring transducer. The force measuring transducer connected with the wheel 124 has an output which varies as a function of the force-applied against the wheel 124 by the section 114 of the suture as the suture is tensioned. The output from the transducer connected with the wheel 124 is also transmitted to the controller 128.

When the output from the transducers indicates that the desired tension is present in the sections 112 and 114 of the suture 110, clamps 132 and 134 are activated to hold the wheels 122 and 124 against rotation and to hold the sections 112 and 114 of the suture 110 against movement relative to the wheels. For example, the suture section 112 is manually pulled and the wheel 122 rotated until the output from the transducer connected with the wheel indicates that a desired tension is present in the section of the suture. The controller 128 then activates the clamp 132 to hold both the wheel 122 and the section 112 of the suture against movement. This results in the desired tension being maintained in the section 112 of the suture. Similarly, when the output from the transducer connected with the wheel 124 indicates to the controller 128 that the desire tension is present in the section 114 of the suture, the clamp 134 is activated to clamp the wheel 124 and suture section 114 against movement.

In response to detecting that the desired tension is present in both sections 112 and 114 of the suture 110, the controller 128 activates a connector assembly 140 (FIG. 6) to press the soft body tissue 102 against the bone 106 with a predetermined force. In response to detecting that the desired tension is present in the sections 112 and 114 of the suture and that the soft body tissue 102 is being pressed against the bone 106 with a desired force, the controller 128 affects operation of the connector assembly 140 to connect the sections 112 and 114 of the suture 110 together.

When the controller detects that the desired tension is present in the sections 112 and 114 of the suture 110, the controller activates an actuator (not shown) to press members 142 and 144 in the connector assembly 140 downward against the body tissue 102 with a predetermined force. While the body tissue 102 is being urged downward with a predetermined force and while a desired tension is being maintained in the sections 112 and 114 of the suture 110, the connector assembly 140 is operated to interconnect the sections 112 and 114 of the suture. The sections 112 and 114 of the suture may be interconnected with a retainer having the same construction as the retainer 82 of FIG. 4. Alternatively, the sections 112 and 114 of the suture may be bonded together. Regardless of how the suture sections are interconnected, a force distribution member may be provided.

To effect a bonding of the sections 112 and 114 of the suture together, the member 142 functions as an anvil and the member 144 functions as a horn to press the two sections 112 and 114 of the suture against each other and at the same time to transmit ultrasonic vibratory energy to at least one of the two sections of the suture. To press the sections 112 and 114 of the suture against each and to apply ultrasonic vibratory energy to the sections of the suture, the anvil 142 is pressed against one side of the suture sections 112 and 114. The horn 144 is pressed against the opposite side of the suture sections 112 and 114.

The specific force with which the horn and anvil 144 and 142 are pressed against opposite sides of the suture sections 112 and 114 will depend upon the composition of the suture sections and the desired extent of deformation of the suture sections. When at least one, and probably both of the suture sections 112 and 114 have been heat softened by ultrasonic vibratory energy, the material of the suture sections 112 and 114 is pliable. The material of the suture sections 112 and 114 then is plastically deformed by the force applied against the-suture sections by the anvil 142 and horn 144.

In addition to the anvil 142 and horn 144, the apparatus for transmitting ultrasonic vibratory energy to the suture sections 112 and 114 includes a generator (not shown) which changes standard electrical power into electrical energy at the desired ultrasonic frequency. A transducer (not shown) changes the electrical energy into low amplitude mechanical motion or vibration. These vibrations are transmitted to a booster which is used to increase or decrease the amplitude of the vibrations. The vibrations are then transmitted to the horn 144.

The ultrasonic vibratory energy transmitted to the suture sections 112 and 114 from the horn 144 is converted into heat energy. When this occurs, the temperature of the material forming the portions of the suture sections 112 and 114 adjacent to the horn 144 increases. As the temperature of the suture sections 112 and 114 increases, the material of the suture sections is heated into the lower end portion of a transition temperature range. As the material of the suture sections 112 and 114 is heated into the transition temperature range, the material softens and becomes pliable. However, the material of the suture sections 112 and 114 does not melt and retains sufficient strength to enable the desired tension to be transmitted through the suture sections.

The somewhat softened material of the heated portions of the suture sections 112 and 114 are pressed together and bond to each other. The materials of the suture sections 112 and 114 are chemically compatible so that a molecular bond can be established between the suture sections. Like materials, that is materials having chemical properties which are the same or very similar will usually bond together. However, dissimilar materials may bond if their melt temperatures are reasonably close and they are of like molecular structure. Generally speaking, amorphous polymers are readily bonded to each other.

One known source of devices for effecting an ultrasonic bond is Dukane Corporation, Ultrasonics Division, 2900 Dukane Drive, St. Charles, Ill. 60174. The connector assembly 140 may have a construction similar to constructions of connector assemblies disclosed in U.S. patent application Ser. No. 09/524,397 filed Mar. 13, 2000 by Peter M. Bonutti et al. and entitled "Method of Using Ultrasonic Vibration to Secure Body Tissue". The disclosure in the aforementioned application Ser. No. 09/524,397 has been and hereby is incorporated herein in its entirety.

Figure 7:
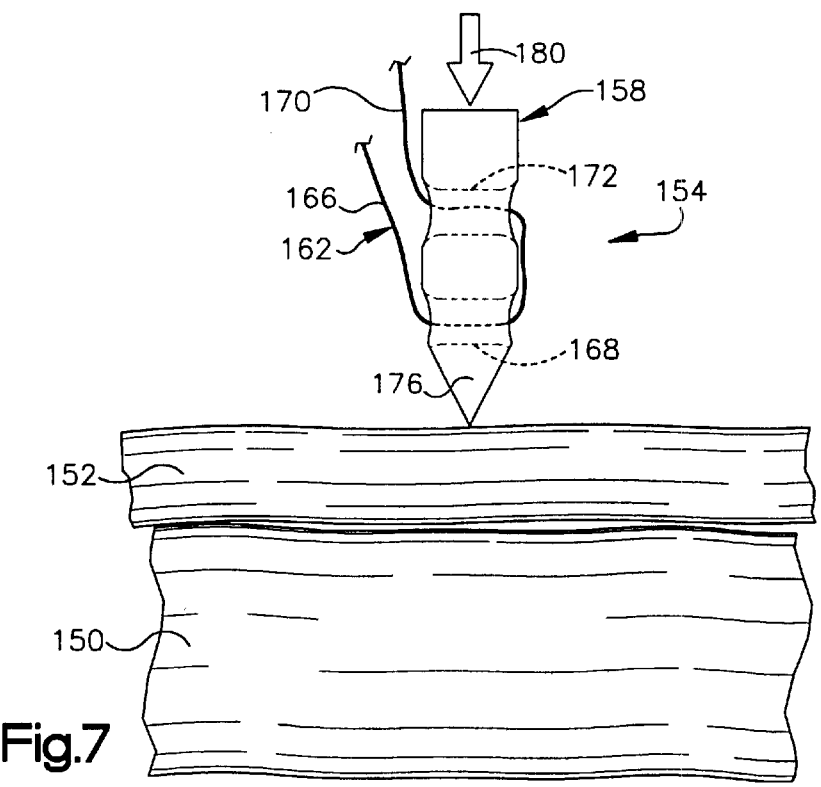
FIG. 7 is a schematic illustration depicting the manner in which the anchor of FIGS. 1 and 2 is positioned relative to layers of soft body tissue prior to securing of the layers of soft body tissue with a suture connected to the anchor.
Figure 8:
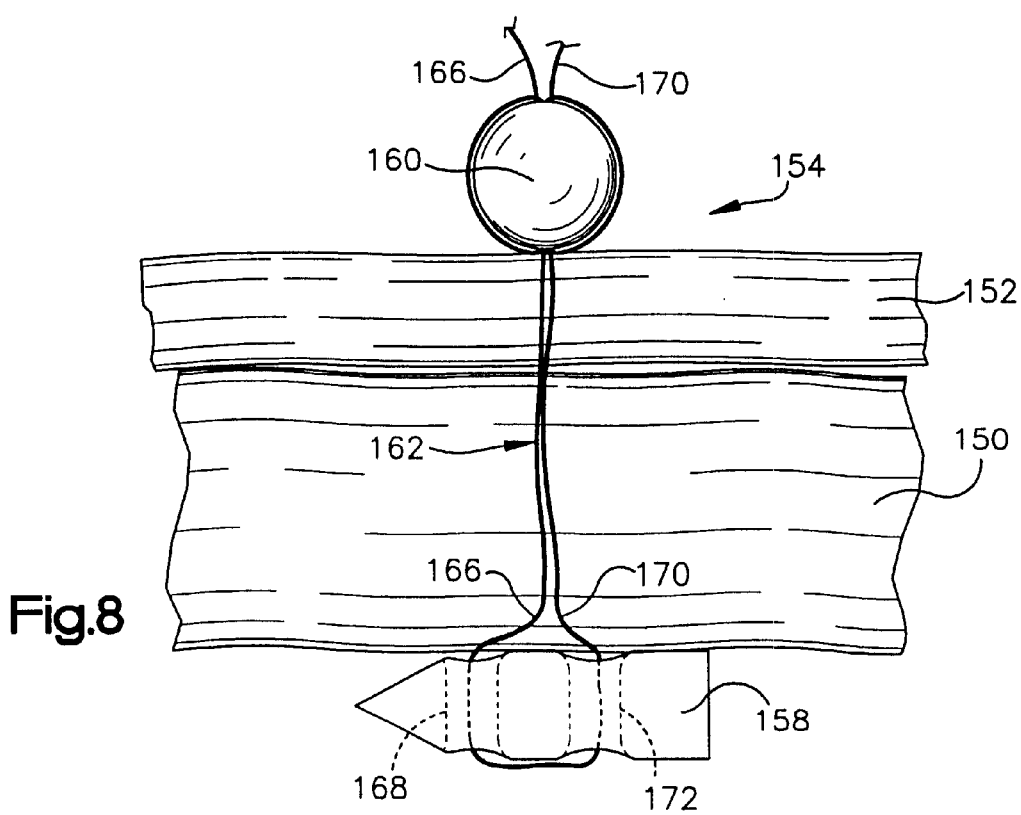
FIG. 8 is a schematic sectional view, generally similar to FIG. 7, illustrating the manner in which the anchor and suture cooperate with a retainer to secure the layers of soft body tissue.

Embodiment of FIGS. 7 and 8

In the embodiments of the invention illustrated in FIGS. 1–6, the anchor has been utilized to secure a suture relative to a bone in a human patient's body. In the embodiment of the invention illustrated in FIGS. 7 and 8, an anchor is utilized to secure a suture relative to soft body tissue in a human patient's body. Since the embodiment of the invention illustrated in FIGS. 7 and 8 is similar to the embodiment of the invention illustrated in FIGS. 1–6, similar terminology will be utilized to identify similar components.

In the embodiment of the invention illustrated in FIGS. 7 and 8, a relatively thick layer of soft body tissue, designated by numeral 150, and a thin layer of soft body tissue, designated by numeral 152, are to be interconnected by a tissue securing system 154. The tissue securing system 154 (FIG. 8) includes an anchor 158 which is connected with a retainer 160 by a suture 162. Although only a single tissue securing system has been disclosed in association with the layers 150 and 152 of soft human body tissue, it is contemplated that a plurality of tissue securing systems could be associated with the layers of human body tissue. The tissue securing systems may be positioned a precise distance from an edge portion of the layers of human body tissue in the manner disclosed in the aforementioned U.S. patent application Ser. No. 09/524,397 filed March 13, 2000 by Peter M. Bonutti et al. and entitled "Method of Using Ultrasonic Vibration to Secure Body Tissue".

The anchor 158 has the same construction as the anchor 20 of FIGS. 1 and 2. The anchor 158 is integrally formed as one piece of freeze dried human bone. The suture 162 has the same construction as the suture 36 of FIGS. 3 and 4. The suture 162 has a cable-like construction with a plurality of interconnected strands formed of the materials previously mentioned in conjunction with the suture 36. The suture 162 has a section 166 which extends from a passage 168 (FIG. 7) in the anchor 158. In addition, the suture 162 has a section 170 which extends from a passage 172 in the anchor 158.

When the anchor 158 is to be positioned relative to the layers 150 and 152 of soft body tissue, a pointed leading end portion 176 is positioned in engagement with one of the layers of body tissue. At this time, a central axis of the anchor 158 extends perpendicular to the layer 152 of body tissue. In the embodiment of the invention illustrated in FIG. 7, the anchor 158 is positioned in engagement with an imperforate surface area on the thin layer 152 of body tissue. However, it is contemplated that the anchor could be inserted from the other side of the two layers of body tissue if desired. If this was done, the anchor 158 would initially be positioned in engagement with an imperforate surface area on the thick layer 150 of body tissue.

Once the anchor 158 has been positioned relative to the layer 152 of body tissue, a force, indicated schematically at 180 in FIG. 7, is applied against a trailing end of the anchor. The force 180 is effective to push the hard cortical bone of the anchor 158 through the two layers 152 and 150 of body tissue. Thus, the force 180 initially presses the pointed leading end portion 176 of the anchor 158 against the thin layer 152 of body tissue. As the anchor 158 moves into the body tissue under the influence of the force 180, the anchor initiates the formation of an opening in the layer 152 of body tissue at a location which is free of openings. The pointed leading end portion 176 of the anchor deflects body tissue sideways to initiate formation of an opening in the layer 152.

Continued movement of the anchor 158 into the layer 152 of body tissue moves the leading end portion 176 of the anchor into engagement with an imperforate surface on the second or lower (as viewed in FIG. 7) layer 150 of body tissue. The leading end portion 176 of the anchor 158 penetrates the layer 150 of body tissue and initiates the formation of an opening under the influence of the continuing force 180. As the anchor moves through the body tissue, the trailing end portion of the anchor moves out of the lower (as viewed in FIG. 7) layer 150 of body tissue. The viscoelastic material of the body tissue resiliently closes behind the anchor 158 as it passes through the body tissue. This results in the layers 150 and 152 of body tissue engaging the two sections 166 and 170 of the suture.

The pointed leading end portion 176 of the anchor 158 is effective to form openings in the layers 150 and 152 of body tissue at locations which were previously free of openings. Thus, the leading end portion 176 of the anchor 158 moves into engagement with an imperforate surface area on an upper or outer side of the thin layer 152 of body tissue and initiates the formation of an opening in the body tissue. Similarly, as the anchor 158 engages the upper side surface of the lower layer 150 of body tissue, the pointed leading end portion 176 initiates the formation of an opening at an imperforate surface area on the lower layer of body tissue. The openings formed by the anchor 158 as it moves through the layers 150 and 152 of body tissue is closed behind the anchor due to the viscoelastic nature of the body tissue.

The anchor 158 can be moved through the layers 150 and 152 of body tissue under the influence of force applied against the trailing end of the anchor by an inserter assembly which may include a sleeve and pusher member, corresponding to the sleeve 58 and pusher member 60 of FIG. 3. The inserter assembly for moving the anchor 158 may have a construction similar to any one of the constructions disclosed in the previously mentioned U.S. Pat. No. 5,948,002 which has been and hereby is incorporated herein.

Once the anchor 158 has been moved through the layers 150 and 152 of body tissue, the section 166 of the suture 162 is tensioned. The anchor 158 and the layers 150 and 152 of body tissue apply sufficient friction against the section 170 of the suture 162 that tensioning the section 166 of the suture is effective to apply a torque to the anchor which rotates it from the orientation illustrated in FIG. 7 to the orientation illustrated in FIG. 8. When the anchor 158 is in the orientation illustrated in FIG. 8, the central axis of the anchor extends generally parallel to the major side surfaces of the layers 150 and 152 of body tissue. At this time, the two sections 166 and 170 of the suture can be tensioned and freely moved relative to the anchor to adjust the relative lengths of the sections 166 and 170 of the suture.

The sections 166 and 170 of the suture are connected with the retainer 160 in the same manner as previously explained in conjunction with the retainer 82 in FIG. 4. In the illustrated embodiment of the retainer 160, the retainer has a spherical configuration with a cylindrical central passage. However, it is contemplated that the retainer 160 could have a configuration of any one of the retainers disclosed in the aforementioned U.S. patent application Ser. No. 09/523,442 filed Mar. 10, 2000 by Peter M. Bonutti et al. and entitled "Method and Apparatus for Securing a Suture". Alternatively, the retainer 160 could have a configuration corresponding to the configuration of any other known retainer.

When the suture 162 has been positioned relative to the retainer, the suture is tensioned with a predetermined tension force. The retainer 160 is then moved along the sections 166 and 170 of the suture and pressed against the layers 152 and 150 of body tissue with a predetermined force. If desired, a force distribution member such as a button, could be provided between the retainer 160 and the layer 152 of body tissue. Another force distribution member could be provided between the anchor 158 and the layer 150 of body tissue.

While the predetermined tension is maintained in the suture 162 and while the retainer 160 is urged toward the body tissue with a predetermined force, the retainer 160 is fixedly connected with the suture 162. The retainer 160 may be fixedly connected with the suture by plastically deforming material of the suture retainer with a cold flowing action or by heating the material of the retainer and plastically deforming the material of the retainer while it is heated into a transition temperature range for the material of the retainer. Heating of the material of the retainer may be accomplished by applying ultrasonic vibratory energy against the suture retainer in the manner disclosed in the aforementioned application Ser. No. 09/524,397, filed Mar. 13, 2000 by Peter M. Bonutti et al. and entitled "Method of Using Ultrasonic Vibration to Secure Body Tissue". Alternatively, the retainer 160 may be connected with the suture 162 in any one of the ways disclosed in the aforementioned U.S. patent application Ser. No. 09/523,442 filed Mar. 10, 2000 by Peter M. Bonutti et al. and entitled "Method and Apparatus for Securing a Suture".

Figure 9:
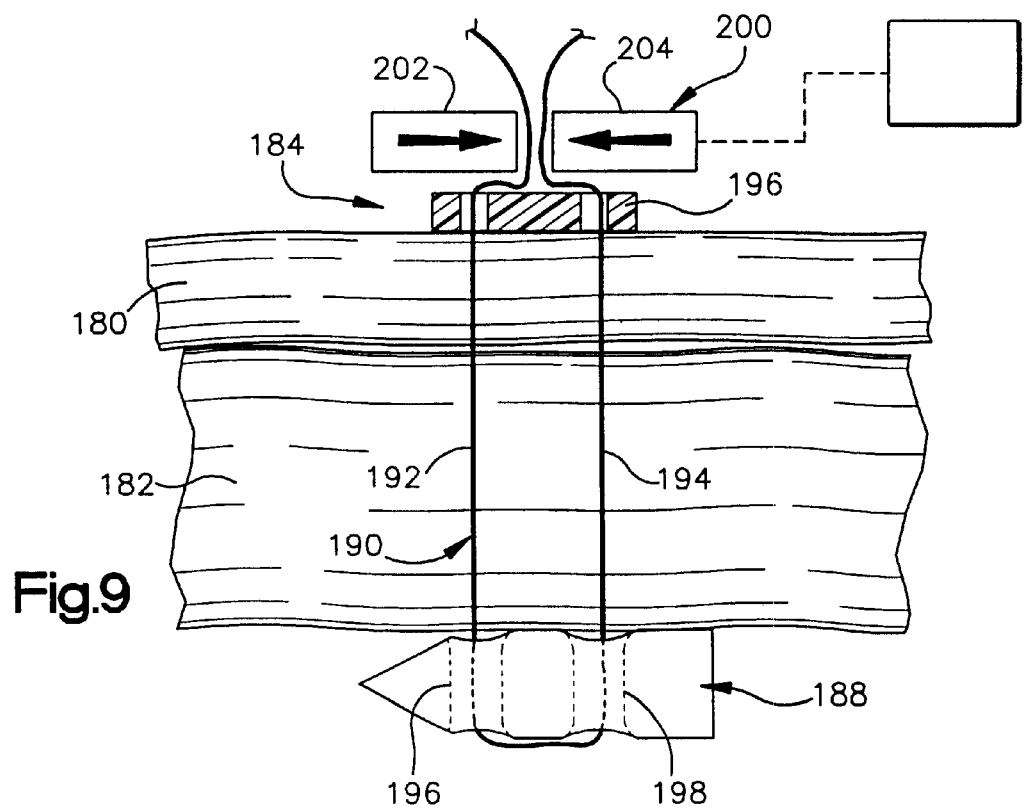
FIG. 9 is a schematic sectional view illustrating the manner in which the anchor and suture of FIG. 7 are utilized to interconnect layers of soft body tissue and the manner in which sections of the suture connected with the anchor are interconnected utilizing ultrasonic vibratory energy.

Embodiment of FIG. 9

In the embodiment of the invention illustrated in FIGS. 7 and 8, a tissue securing system 154 is utilized to interconnect layers 150 and 152 of body tissue. A retainer 160 is associated with a suture to apply a predetermined force against the layers 150 and 152 of body tissue and to maintain a predetermined tension in the sections 166 and 170 of the suture. In the embodiment of the invention illustrated in FIG. 9, the suture retainer is omitted and the sections of the suture are connected directly to each other. Since the embodiment of the invention illustrated in FIG. 9 is similar to the embodiments of the invention illustrated in FIGS. 1–8, similar terminology will be utilized to identify similar components. It should be understood that one or more of the features of the embodiments of the invention illustrated in FIGS. 1–8 could be utilized in association with the embodiment of the invention illustrated in FIG. 9.

In the embodiment of the invention illustrated in FIG. 9, soft tissue layers 180 and 182 are disposed in linear apposition with each other. A tissue securing system 184 is utilized to interconnect the layers 180 and 182 of soft human body tissue. The tissue securing system 184 includes an anchor 188 and a suture 190. The anchor 188 has the same construction as the anchor 20 of FIGS. 1 and 2. The specific anchor 188 illustrated in FIG. 9 is formed as one piece of freeze dried human bone. The suture 190 has the same construction as the suture 36 of FIGS. 3 and 4.

The suture 190 is connected with the anchor in the same manner as previously described in conjunction with the embodiment of the invention illustrated in FIGS. 7 and 8. The suture 190 has sections 192 and 194 which extend from passages 196 and 198 through the layers 180 and 182 of body tissue. In the embodiment of the invention illustrated in FIG. 9, a force distribution member or button 196 is provided adjacent to the upper (as viewed in FIG. 9) major side surface of the layer 180 of tissue. The force distribution member 198 distributes force transmitted from the suture 190 over a relatively large area on the layer 180 of tissue.

The two sections 192 and 194 of the suture are tensioned with a predetermined tension force. The force distribution member 196 is pressed against the layer 180 of body tissue with a predetermined force. While the predetermined tension is maintained in the suture 190 and while the force distribution member 196 is pressed against the layer 180 of tissue with a predetermined force, the two sections 192 and 194 of the suture 190 are bonded to each other by a connector assembly 200.

The connector assembly 200 may have the same construction as previously described in conjunction with the embodiment of the invention illustrated in FIG. 6. Of course, the connector assembly 200 may have a construction which is different than the construction of the connector assembly 140 of FIG. 6. If desired, the two sections 192 and 194 of the suture 190 may be tensioned with a predetermined force by an apparatus having the same construction as the apparatus 120 of FIG. 6. It should be understood that the two sections 192 and 194 of the suture 190 may be tensioned in a different manner if desired. For example, the suture sections 192 and 194 could be manually tightened without using the apparatus 120 of FIG. 6.

The connector assembly 200 includes an anvil 202 which is pressed against one side of the sections 192 and 194 of the suture 190. A horn 204 is pressed against the opposite sides of the sections 192 and 194 of the suture 190. While the horn and anvil 202 and 204 are being pressed against opposite sides of the sections 192 and 194 of the suture 190, ultrasonic vibratory energy is transmitted from the horn 204 to at least one of the sections of the suture. The ultrasonic vibratory energy transmitted from the horn 204 to the sections 192 and 194 of the suture 190 is effective to heat the material of the sections of the suture into their transition temperature range as the sections of the suture are pressed against each other.

When the sections of the suture have been heated into their transition temperature range, they are bonded to each other. The extent to which the sections 192 and 194 of the suture 190 are heated is sufficient to soften the material of the suture. However, the sections 192 and 194 of the suture are not heated to a temperature which is so great as to impair the strength of the suture 190. This enables the desired tension force to continue to be transmitted through the sections 192 and 194 of the suture 190 as they are bonded to each other by the anvil 202 and horn 204 of the connector assembly 200. The manner in which the connector assembly 200 interconnects the sections 192 and 194 of the suture 190 is the same as is disclosed in the aforementioned U.S. patent application Ser. No. 09/524,397 filed March 13, 2000 by Peter M. Bonutti et al. and entitled "Method of Using Ultrasonic Vibration to Secure Body Tissue".

Figure 10:
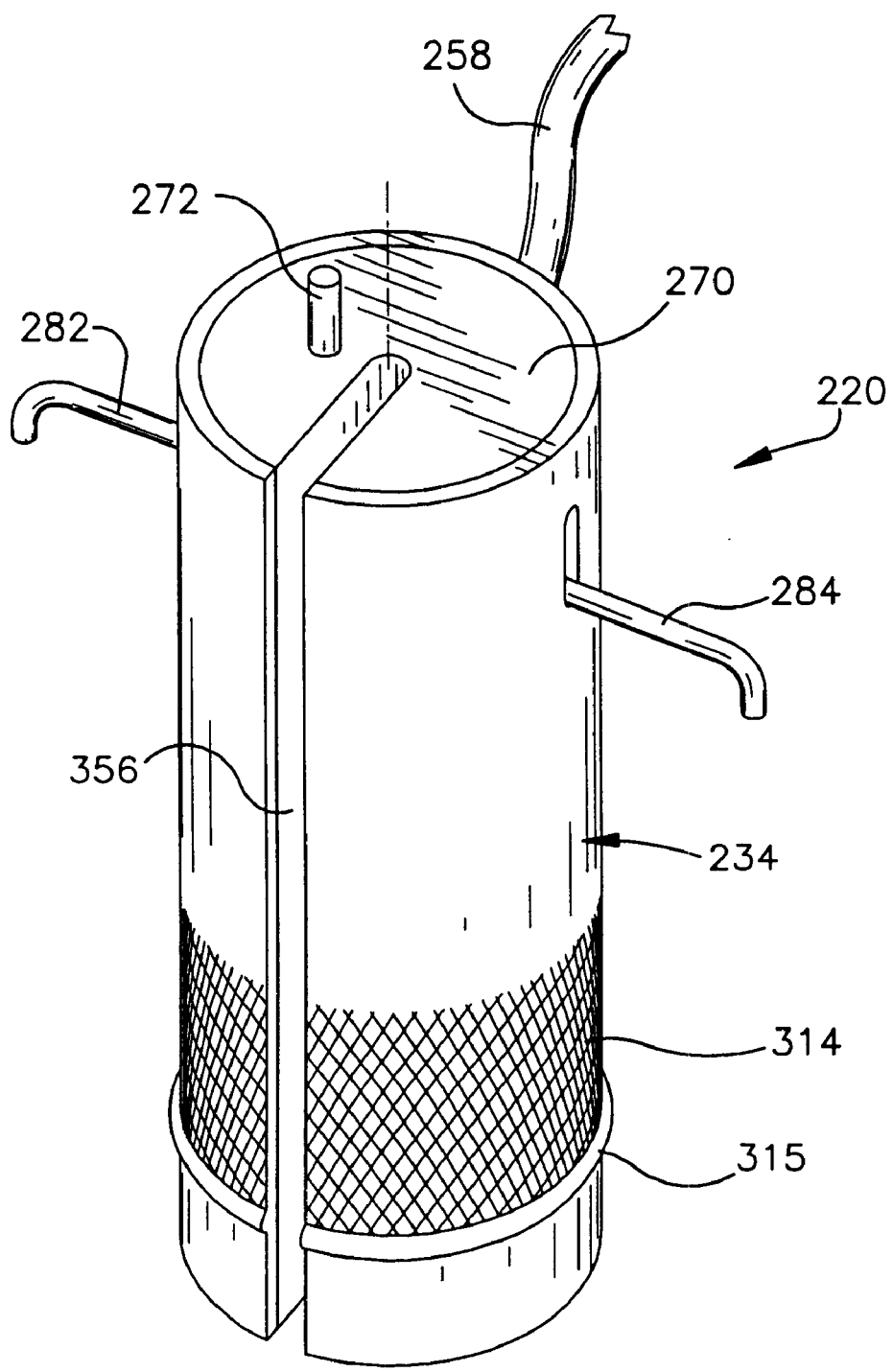
FIG. 10 is a schematic pictorial illustration of an apparatus for use in tensioning a suture with a predetermined tension, applying a predetermined force against a retainer, and connecting the retainer with the suture.
Figure 11:
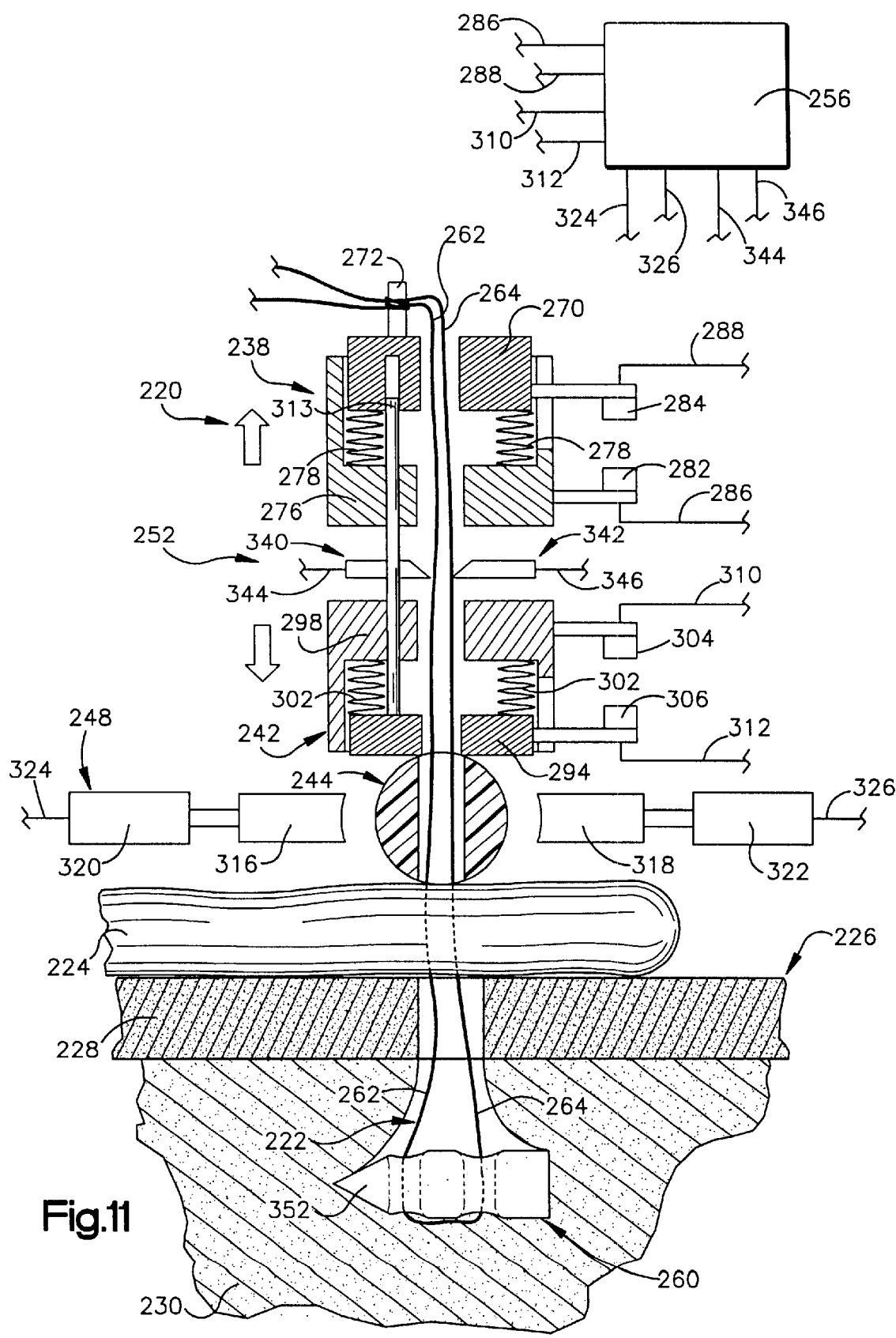
FIG. 11 is a highly schematicized illustration depicting the manner in which the apparatus of FIG. 10 is utilized to tension a suture with a predetermined force, apply a predetermined force against a retainer, and connect the retainer with the suture.

Embodiment of FIGS. 10 and 11

In the embodiments of the invention illustrated in FIGS. 1–9, a suture is tensioned with a desired force and a desired force is transmitted to body tissue before a retainer is connected with the suture (FIGS. 4 and 8) or sections of the suture are connected together (FIGS. 6 and 9). An apparatus for use in tensioning the suture and effecting the transmittal of force to body tissue is illustrated in FIGS. 10 and 11. Although the apparatus of FIGS. 10 and 11 is advantageously used with a retainer, the apparatus may be used without a retainer if desired. Since the embodiment of the invention illustrated in FIGS. 10 and 11 is similar to the embodiments of the invention illustrated in FIGS. 1–9, similar terminology will be utilized to identify similar components. It should be understood that one or more features of the embodiments of the invention illustrated in FIGS. 1–9 may be used with the embodiment of the invention illustrated in FIGS. 10 and 11.

An apparatus 220 (FIGS. 10 and 11) is utilized to secure a suture 222 (FIG. 11) relative to body tissue. The suture 222 may have the same construction as the suture 36 if FIGS. 3 and 4. The specific suture 222 is a cable with a plurality of interconnected strands or filaments. However, the suture 222 could be formed of a single strand if desired.

In the embodiment of the invention illustrated in FIG. 11, the body tissue includes soft body tissue 224 and bone 226. The bone 226 includes a compact outer layer 228 which encloses cancellous bone 230. Although the apparatus 220 has been illustrated in FIG. 11 in association with soft body tissue 224 and bone 226, it is contemplated that the apparatus 220 could be utilized in association with just soft tissue in the manner illustrated in FIG. 8. Alternatively, the apparatus 220 could be utilized with just hard tissue. Thus, the apparatus 220 could be utilized with fragments of a bone or with separate bones if desired.

The apparatus 220 includes a housing 234 (FIG. 10). In FIG. 11, the housing has been omitted and the apparatus enclosed by the housing has been illustrated schematically. The apparatus 220 (FIG. 11) includes a suture tensioning assembly 238. The suture tensioning assembly 238 is operable to tension the suture 222 with a predetermined tension force.

The apparatus 220 also includes a force application assembly 242 (FIG. 11). The force application assembly 242 is operable to apply a predetermined force to a retainer 244 to urge the retainer toward the soft body tissue 224 and bone 226. The suture tensioning assembly 238 is disposed in the upper end portion of the housing 234 (FIG. 10) and the force application assembly 242 is disposed in the lower end portion of the housing.

A connector assembly 248 (FIG. 11) is provided in the lower end portion of the housing 234 adjacent to the force application assembly 242. The connector assembly 248 is operable to connect the retainer 244 with the suture 242. A predetermined tension force is applied to the suture 242 by the suture tensioning assembly 238 and a predetermined force is transmitted from the force application assembly 242 through the retainer 244 to the soft body tissue 224 and bone 226 when the connector assembly 248 is operated to connect the retainer with the suture.

A trimmer assembly 252 (FIG. 11) is provided in the housing 234 (FIG. 10). The trimmer assembly 252 is disposed between the suture tensioning assembly 238 and force application assembly 242. The trimmer assembly 252 is operable to sever the suture 222 after the connector assembly 248 has connected the retainer 244 with the suture and while the predetermined tension is present in the suture and a predetermined force is being transmitted from the retainer through the body tissue 224.

Operation of the connector assembly 248 and trimmer assembly 252 is controlled by a microprocessor or controller 256. The controller 256 detects when the predetermined tension is present in the suture 222 and when the predetermined force is transmitted through the retainer 244 to the soft body tissue 224 and bone 226. In response to detection of the predetermined tension in the suture 222 and the transmission of the predetermined force to the retainer 244, the controller 256 initiates operation of the connector assembly 248 to connect the retainer 244 with the suture 222. Immediately thereafter, the controller 256 effects operation of the trimmer assembly 252 to sever the suture 222.

In the embodiment of the invention illustrated in FIGS. 10 and 11, the controller 256 (FIG. 11) effects operation of the connector assembly 248 when both a predetermined tension is present in the suture 222 and a predetermined force is being transmitted through the retainer to the body tissue 224 and bone 226. However, it is contemplated that the apparatus 220 could be constructed in such a manner as to have the controller 256 effect operation of the connector assembly 248 in response to only detection of a predetermined tension in the suture 222. Alternatively, the controller 256 could effect operation of the connector assembly 248 in response to only detection of transmission of a predetermined force to the retainer 244 and body tissue 224.

In the embodiment of the invention illustrated in FIGS. 10 and 11, the controller 256 (FIG. 11) is spaced from the housing 234 (FIG. 10). The controller 256 is connected with the apparatus disposed in the housing through a cable 258. However, it is contemplated that the controller 256 could, if desired, be mounted on or in the housing 234.

In the embodiment of the invention illustrated in FIG. 11, the suture 222 is connected with an anchor 260 which is embedded in the cancellous bone 230 in a spaced apart relationship with the compact outer layer 228 of the bone 226. The anchor 260 has the same construction as the anchor 20 of FIGS. 1 and 2. Sections 262 and 264 of the suture 222 extend from passages in the anchor through the compact outer layer 228 of the bone 226 and the soft body tissue 224 to the retainer 244. The sections 262 and 264 of the suture 222 extend through the force transmission assembly 242 and trimmer assembly 252 to the suture tensioning assembly 238.

Although the suture 222 is connected with the anchor 260 in the embodiment of the invention illustrated in FIG. 11, it is contemplated that the suture 222 could be connected with body tissue in a manner other than through the use of the anchor 260. For example, suture 222 could be connected with body tissue in any one of the ways disclosed in the aforementioned U.S. patent application Ser. No. 09/523,442 filed Mar. 10, 2000 by Peter M. Bonutti et al. and entitled "Method and Apparatus for Securing a Suture".

Of course, the suture 222 could be connected with either hard or soft body tissue in other known ways if desired. For example, the suture could be connected with body tissue in any one of the ways disclosed in the aforementioned U.S. Pat. No. 5,928,267. It is contemplated that the apparatus 220 will be utilized in association with sutures which are connected with many different types of body tissue in many different ways.

The suture tensioning assembly 238 is operable to tension the suture 222 with at least a predetermined tension force. The suture tensioning assembly 238 includes a circular upper member 270 having an opening through which the sections 262 and 264 of the suture 222 extend. The upper member 270 is movable downward relative to the housing 234 from the uppermost position illustrated in FIG. 10. Although the upper member 270 can move downward from the position shown in FIGS. 10 and 11, the upper member can not move upward from the position shown in FIGS. 10 and 11.

The sections 262 and 264 of the suture 222 are fixedly secured to the upper member 270. In the embodiment of the invention illustrated in FIG. 11, a pin 272 extends upward from the upper member 270. The sections 262 and 264 of the suture 222 are tied to the pin 272.

It should be understood that the sections 262 and 264 of the suture 222 could be connected with the upper member 270 in a different manner if desired. For example, the sections 262 and 264 of the suture could be locked in a V-shaped slot formed in the upper member 270. Alternatively, a gripper assembly could be provided on the upper member 270 to grip the sections 262 and 264 of the suture.

A circular lower member 276 in the suture tensioning assembly 238 (FIG. 11) is connected with the upper member 270 by a plurality of springs which have been illustrated schematically at 278 in FIG. 11. The lower member 276 is movable relative to the housing 234. The lower member 276 can only move upward from the position shown in FIGS. 10 and 11. When the lower member 276 moves upward, the springs 278 are compressed.

A pair of manually engageable handles 282 and 284 (FIG. 10) are fixedly connected with diametrically opposite sides of the cylindrical lower member 276. The handles 282 and 284 extend through slots in the housing 234 and are readily engaged by fingers on the hand of a surgeon during use of the apparatus 220. The handles 282 and 284 can be manually moved upward (as viewed in FIG. 10) to move the lower member 276 upward relative to the housing 234. The handles 282 and 284 are engagable with lower ends of the slots in the housing to block downward movement of the lower member 276 from the position shown in FIG. 11.

In order to tension the suture 222, the sections 262 and 264 of the suture are first tied off at the pin 272. As the sections 262 and 264 of the suture 222 are tied off at the pin 272, an initial tension force is transmitted from the suture to the upper member 270. This initial tension force moves the upper member 270 downward and slightly compress the springs 278. The handles 282 and 284 are pressed against lower ends of the slots in the housing 234 to resist the initial tension force.

Fingers on one hand of the surgeon then apply an upwardly directed force against the handles 282 and 284. This upwardly directed force is applied against the springs 278 (FIG. 10) by the lower member 276. The upwardly directed force is transmitted through the springs 278 to the upper member 270 and the sections 262 and 264 of the suture 222. As the force applied against the handles 282 and 284 (FIG. 10) is increased, the springs 278 are compressed and the tension in the sections 262 and 264 of the suture 222 is increased.

As the springs 278 are compressed, a movable contact 282 (FIG. 11) moves upward toward a second contact 284. The movable contact 282 is fixedly connected to the lower member 276. The second contact 284 is fixedly connected to the upper member 270. The movable contact 282 moves upward into engagement with the second or upper contact 284 when the springs 278 have been compressed to a predetermined extent by movement of the lower member 276 toward the upper member 270. When the springs 278 have been compressed to the predetermined extent, a predetermined force is transmitted from the lower member 276 to the upper member 270. This predetermined force is transmitted to the sections 262 and 264 of the suture through the pin 272 connected with the upper member 270.

When the movable contact 282 engages the second contact 284 and the predetermined tension force is present in the suture 222, a circuit is completed between conductors 286 and 288 connected with the movable contact 282 and second contact 284. The conductors 286 and 288 are connected with the controller 256. This enables the controller 256 to detect when the movable contact 282 engages the second or upper contact 284 and when the predetermined tension is present in the suture 222. The controller 256 provides a visual and/or an audible signal to indicate to the surgeon that the predetermined tension force is being applied to the sections 262 and 264 of the suture 222.

The force application assembly 242 is operable to apply at least a predetermined force to the retainer 244. This predetermined force urges the retainer toward the soft body tissue 224 and bone 226. The force transmitted from the retainer 244 to the soft body tissue 224 is effective to compress the soft body tissue against the bone 226.

The force application assembly 242 includes a circular lower member 294 which is located at the lower end of the housing 234 (FIG. 10). The lower member 294 is movable upward from its lowermost position shown in FIG. 11. The lower member 294 is engageable with the retainer 244. The lower member 294 may have a lower (as viewed FIG. 11) side surface which is shaped to provide a recess in which the upper portion of the retainer 244 is received. Thus, although the lower member 294 is illustrated in FIG. 11 as having a flat circular lower side surface, the lower member 294 could have a concave surface with an arc of curvature which corresponds to the arc of curvature of the spherical retainer 244.

An upper member 298 in the force application assembly 242 has a generally cylindrical configuration and is disposed in a coaxial relationship with the lower member 294. The upper member 298 is fixedly connected with the housing 234 (FIG. 10). The lower member 294 is axially movable relative to the housing 234. The lower member 294 is connected with the upper member 298 by a plurality of springs which have been illustrated schematically at 302 in FIG. 11.

An upper contact 304 is fixedly connected with the upper member 298. A lower or movable contact 306 is connected with the lower member 294. The upper contact 304 is connected with the controller 256 by a conductor 310. The movable contact 306 is connected with the controller 256 by a conductor 312.

A guide rod 313 extends between the lower member 294 in the force application assembly 242 and the upper member 270 in the suture tensioning assembly 238. The guide rod interconnects the suture tensioning assembly 238 and the force application assembly 242. In addition, the guide rod guides relative movement between the upper member 270 and lower member 276 in the suture tensioning assembly 238 and relative movement between the upper member 298 and lower member 294 in the force application assembly 242. Although only a single guide rod 313 has been illustrated in FIG. 11, it should be understood that a plurality of guide rods are provided in the apparatus 220.

When a predetermined force is to be transmitted through the retainer 244 to the body tissue 224 and bone 226, a knurled handle portion 314 (FIG. 10) of the housing 234 is manually grasped. A collar 315 may be provided adjacent to the lower end of the handle portion 315. Force is manually applied to the housing 234 urging the housing downward (as viewed in FIG. 11) toward the retainer 244. At the same time, an upward force is being manually applied against the handles 282 and 284.

The downward force which is manually applied to the housing 234 is transmitted to the upper member 298 (FIG. 11) which is fixedly connected with the housing. This downward force is transmitted from the upper member 298 through the springs 302 to the lower member 294. The lower member 294 transmits the force to the retainer 244 which is pressed against the soft body tissue 224.

As the housing 234 and upper member 298 are manually urged downward toward the retainer 244, the springs 302 (FIG. 11) are compressed. As the springs 302 are compressed, the upper contact 304 approaches the lower contact 306. When the springs 302 have been compressed to a predetermined extent, a predetermined force is transmitted from the upper member 298 through the springs 302 and lower member 294 to the retainer 244 and body tissue 224. As this occurs, upper contact 304 engages the lower contact 306.

Engagement of the contacts 304 and 306 completes a circuit which enables the controller 256 to detect that at least a predetermined force has been transmitted from the force application assembly 242 to the retainer 244 and the body tissue 224 and bone 226.

When the controller 256 detects both the presence of the predetermined tension in the suture 222 and the application of the predetermined force against the retainer 244, the controller initiates operation of the connector assembly 248 to connect the retainer with the suture. The connector assembly 248 includes a pair of movable members 316 and 318 which are disposed adjacent to diametrically opposite sides of the retainer 244. An actuator 320 is connected with the movable member 316. An actuator 322 is connected with the movable member 318. The actuators 320 and 322 are connected with the controller 256 by conductors 324 and 326.

In the embodiment of the invention illustrated in FIG. 11, the actuators 320 and 322 are operable to press the movable members 316 and 318 against opposite sides of the retainer 244 and to effect plastic deformation of the material of the retainer 244. Force applied against opposite sides of the retainer 244 by the members 316 and 318 is effective to cause cold flowing of the material of the retainer at a temperature below a transition temperature range for the material of the retainer. The cold flowing of the material of the retainer 244 results in a collapsing of a passage in the retainer through which the sections 262 and 264 of the suture extend. As the passage through the retainer 244 collapses and the material of the retainer cold flows, the material flows around the sections 262 and 264 of the suture 222. This enables the material of the retainer 244 to bond to and obtain a firm grip on the suture 222.

In the embodiment of the invention illustrated in FIG. 11, the sections 262 and 264 of the suture 222 extends straight through the passage in the retainer 244. However, if desired, the sections 262 and 264 of the suture 222 could be wrapped around the retainer. If this was done, the force applied against the sections of the suture and the retainer 244 would embed the suture turns around the outside of the retainer 244 in the material of the retainer and enhance the grip between the suture 222 and the retainer 244.

During the time in which the force application members 316 and 318 are applying clamping forces against opposite sides of the retainer 244, the retainer is pressed against the upper side surface of the body tissue 224 with a predetermined force. In addition, a predetermined tension is maintained in the sections 262 and 264 of the suture 222.

In the embodiment of the invention illustrated in FIG. 11, clamping forces have been applied against opposite sides of the retainer 244 to cause cold flowing of the material of the retainer. However, if desired, the connector assembly 248 could be constructed so as to effect heating of the material of the retainer 244 by the application of ultrasonic vibratory energy to the retainer. The frictional heat created by the ultrasonic vibratory energy transmitted to the suture retainer 244 is effective to heat the material of the suture retainer into a transition temperature range to facilitate collapsing of the passage in the retainer and to facilitate bonding of the material of the retainer with the sections 262 and 264 of the suture 222. If the connector assembly 248 is to be constructed so as to apply ultrasonic vibratory energy to the retainer 244, the movable member 316 could be an anvil which engages one side of the retainer and the movable member 318 could be a horn which applies ultrasonic vibratory energy to the retainer.

Once the retainer 244 has been securely connected with the sections 262 and 264 of the suture 222, the trimmer assembly 252 is operated to sever the sections 262 and 264 of the suture. The trimmer assembly 252 is operable to sever the sections 262 and 264 of the suture 222 at a location disposed between the suture tensioning assembly 238 and the force application assembly 242. Since the retainer 244 has been securely connected to the suture before the trimmer assembly 252 is operated, the retainer is effective to maintain the predetermined tension in the sections 262 and 264 of the suture which extend between the retainer and the anchor 260. In addition, the retainer 244 is effective to apply the predetermined force against the body tissue 224.

The trimmer assembly 252 includes a pair of cutter assemblies 340 and 342. The cutter assemblies 340 and 342 are connected with the controller 256 by conductors 344 and 346. After completion of operation of the connector assembly 248 to connect the retainer 244 with the sections 262 and 264 of the suture 222, the controller 256 initiates operation of the cutter assemblies 340 and 342 in the trimmer assembly 252 to sever the sections 262 and 264 of the suture 222.

When the suture 222 (FIG. 11), anchor 260 and retainer 244 are to be utilized to secure the soft body tissue 224 with the bone 226, the suture 222 is inserted through the passages in the anchor 260 in the manner previously explained in conjunction with the embodiment of the invention illustrated in FIGS. 1–4. When this has been done, a pointed end portion 352 of the anchor 260 is positioned relative to the soft body tissue 224 while the soft body tissue is in a desired location relative to the bone 226 in the manner illustrated schematically in FIG. 3. An inserter assembly is then utilized to move the anchor 20 through the body tissue 224 and into the bone 226. When the anchor has been moved to a predetermined depth in the cancellous bone 230, the anchor is toggled from an orientation similar to the orientation illustrated in FIG. 3 to the orientation illustrated in FIG. 11.

Once the anchor 260 and suture 222 have been positioned relative to the body tissue 224 and bone 226, the retainer 244 is slid along the sections 262 and 264 of the suture into engagement with the body tissue 224. The suture sections 262 and 264 are then positioned in the apparatus 220 (FIG. 10). A slot 356 is formed in the apparatus 220 to facilitate positioning of the sections 262 and 264 of the suture in the apparatus. The slot 256 extends through the housing to central portions of the suture tensioning assembly 238 (FIG. 11), force application assembly 242, connector assembly 248, and trimmer assembly 252. Although it is believed that it will be preferred to utilize the slot 356 to facilitate positioning of the suture 222 relative to the apparatus 220, a passage could be provided through the apparatus and the sections 262 and 264 of the suture inserted through the passage.

Once the sections 262 and 264 of the suture 222 have been positioned in the apparatus 220, the apparatus is moved along the suture 222 into engagement with the retainer 244. While the apparatus 220 is pressed firmly against the retainer 244, the sections 262 and 264 of the suture are tied to the pin 272. At this time, there will be some tension in the sections 262 and 264 of the suture 222 and there will be some force transmitted from the force application assembly 242 to the retainer 244. However, the tension in the suture and the force transmitted to the retainer will be less than a minimum desired tension and force.

In order to effect the transmission of the desired force from the apparatus 220 through the retainer 244 to the soft body tissue 224 and bone 226, a surgeon manually grasps the handle portion 314 (FIG. 10) of the housing 234 with one hand and pushes the housing toward the retainer 244 (FIG. 11). As this occurs, the springs 302 in the force application assembly are compressed and the contact 304 moves into engagement with the contact 306 to indicate to the controller that the predetermined force is being transmitted from the apparatus 220 to the retainer 244. At this time, the controller 256 may provide a visual and/or audible indication to the surgeon that a predetermined force has been transmitted through the retainer 244 to the body tissue 224.

The surge on then grasps the handles 282 and 284 (FIG. 10) with the other hand and pulls the handles upward. As this occurs, the springs 278 in the suture tensioning assembly 238 are compressed and force is applied against the upper member 270 to increase the tension in the suture sections 262 and 264. When a predetermined tension is present in the suture sections 262 and 264, the lower contact 282 in the suture tensioning assembly 238 is in engagement with the upper contact 284 to provide an indication to the controller that the predetermined tension is present in the suture. At this time, the controller 256 may provide a second visual or audible signal to the surgeon.

When the predetermined tension is present in the sections 262 and 264 of the suture 222 and the predetermined force is being transmitted from the retainer 244 to the soft body tissue 224 and bone 226, the controller 256 effects operation of the connector assembly 248 to securely connect the retainer 244 with the sections 262 and 264 of suture. After the retainer 244 has been connected with the sections 262 and 264 of the suture, the controller 256 effects operation of the trimmer assembly 252 to sever the sections 262 and 264 of the suture. This enables the apparatus 220 to be moved away from the body tissue 224.

Figure 12:
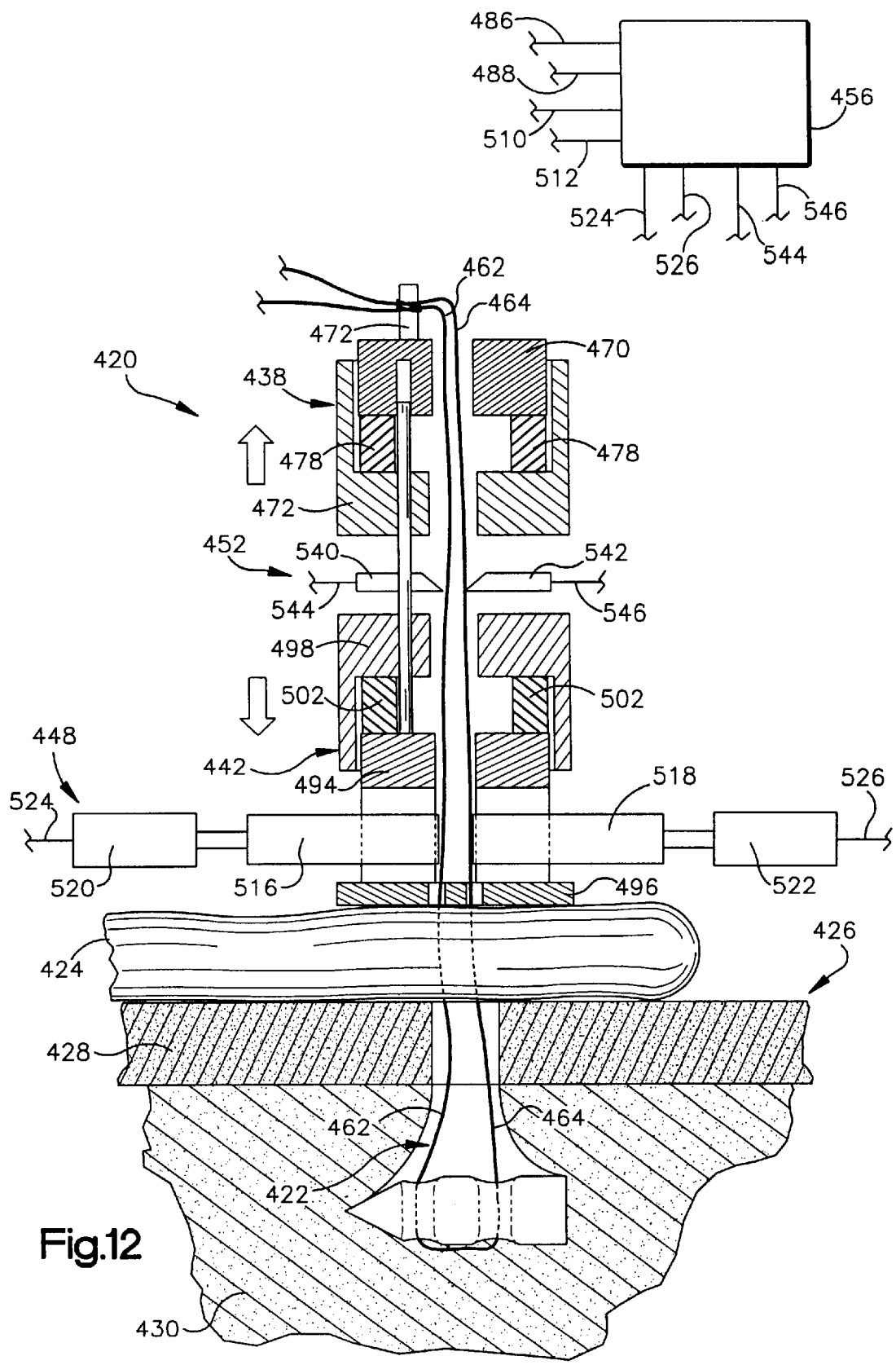
FIG. 12 is a highly schematicized illustration of a second embodiment of the apparatus of FIG. 11.

Embodiment of FIG. 12

In the embodiment of the invention illustrated in FIG. 11, a suture retainer 244 is connected with the sections 262 and 264 of the suture 222. In the embodiment of the invention illustrated in FIG. 12, the sections of the suture are connected to each other. Since the embodiment of the invention illustrated in FIG. 12 is similar to the embodiments of the invention illustrated in FIGS. 1–11, similar terminology will be utilized to identify similar components. It should be understood that one or more features of the embodiments of the invention illustrated in FIGS. 1–11 may be used with the embodiment of the invention illustrated in FIG. 12.

The apparatus 420 is utilized to secure a suture 422 relative to soft body tissue 424 and a bone 426. The suture 422 may have the same construction as the suture 36 of FIGS. 3 and 4. The specific suture 422 is a monofilament having a continuous cylindrical outer side surface. However, the suture 422 may be formed a plurality of intertwined strands or filaments.

The bone 426 includes a compact outer layer 428 which encloses cancellous bone 430. Although the suture 422 has been illustrated schematically in FIG. 12 as being associated with soft body tissue 424 and a bone 426, it is contemplated that the suture could be associated with just soft body tissue or with two portions of a bone or two bones. It should be understood that the suture 422 could be associated with body tissue in any desired way.

The apparatus 420 includes a suture tensioning assembly 438 which is operable to tension the suture 422 with a predetermined tension force. The apparatus 420 also includes a force application assembly 442 which is operable to transmit a predetermined force to the soft tissue 424 and bone 426. The apparatus 420 also includes a connector assembly 448.

The connector assembly 448 is operable to connect sections 462 and 464 of the suture with each other while a predetermined tension force is being transmitted through the sections of the suture and while a predetermined force is being transmitted to the soft tissue 424 and bone 426. Thus, the connector assembly 448 is operable to connect the two sections 462 and 464 of the suture 422 with each other while the suture tensioning assembly 438 tensions the suture to provide a tension force of at least a predetermined magnitude in the sections 462 and 464 of the suture. In addition, the connector assembly 448 is operable to connect the sections 462 and 464 of the suture 422 together while the force application assembly 442 is operable to transmit at least a predetermined force to the soft tissue 424 and bone 426.

A trimmer assembly 452 is operable to sever the sections 462 and 464 of the suture 422 while the predetermined tension force is present in the sections of the suture and while the predetermined force is transmitted to the soft tissue 424.

A controller 456 effects operation of the connector assembly 448 to connect the suture sections 462 and 464 together in response to both detection that at least a predetermined tension force is present in the sections 462 and 462 of the suture and detection that at least a predetermined force is being transmitted to the soft tissue 424 and bone 426. The suture tensioning assembly 438, force application assembly 442, connector assembly 448, and trimmer assembly 452 are at least partially enclosed by a housing which corresponds to the housing 234 of FIG. 10. The controller 456 is connected with the housing by a suitable cable, corresponding to the cable 258 of FIG. 10. However, the controller could be mounted in or on the housing for the apparatus 420 if desired.

It should be understood that the suture tensioning assembly 438 of FIG. 12 corresponds to the suture tensioning assembly 238 of FIG. 11. Similarly, the force application assembly 442 of FIG. 12 corresponds to the force application assembly 242 of FIG. 11. The connector assembly 448 of FIG. 12 corresponds to the connector assembly 248 of FIG. 11. The trimmer assembly 452 of FIG. 12 corresponds to the trimmer assembly 252 of FIG. 11.

The suture tensioning assembly 438 (FIG. 12) includes a circular upper member 470 and a circular lower member 472. In accordance with a feature of the embodiment of the invention illustrated in FIG. 12, force transducers 478 interconnect the upper and lower members 472. The force transducers 478 are connected with the controller 456 by leads 486 and 488.

Although the force transducers 478 could have many different constructions, it is contemplated that they may be piezoelectric transducers having a piezoelectric crystal as a sensitive element. The piezoelectric crystals in the force transducers 478 have outputs which correspond to the magnitude of the force being transmitted from the lower member 422 through the force transducers 478 to the upper member 470.

The sections 462 and 464 of the suture 422 are secured to a pin 472 extending upward from the upper member 470. Therefore, force transmitted from the lower member 472 to the upper member 470 is transmitted from the upper member through the pin 472 to the suture sections 462 and 464. The output from the force transducers 478 indicates to the controller 456 when a predetermined tension force has been transmitted from the lower member 472 through the force transducers 478 and upper member 470 to the sections 462 and 464 of the suture 422.

A pair of handles (not shown), corresponding to the handles 282 and 284 of FIG. 10, are connected with the lower member 472. The handles connected with the lower member 472 are manually engageable. Force which is manually applied to the handles is transmitted from the lower member 472 through the force transducers 478 to the upper member 470.

The force application assembly 442 is operable to transmit a predetermined force to the soft tissue 424 and bone 426. The force application assembly 442 includes a cylindrical lower member 494 which extends downward into engagement with a force distribution member 496 which is disposed on the soft tissue 424. The force distribution member or button 496 has a generally circular configuration with a pair of passages through which the sections 462 and 464 of the suture 422 extend. If desired, the force distribution member 496 could be eliminated.

The force application assembly 494 also includes a cylindrical upper member 498. The upper member 498 is connected with the housing (not shown) which encloses the apparatus 420 and corresponds to the housing 234 of FIG. 10.

The upper member 498 is connected with the lower member 494 by a plurality of force transducers 502. The force transducers 502 are connected with the controller 456 through conductors 510 and 512. The output from the force transducers 502 corresponds to the magnitude of the force transmitted from the upper member 498 to the lower member 494.

Although the force transducers 502 may have many different constructions, in one specific embodiment of the invention, the force transducers 502 were piezoelectric transducers having a piezoelectric crystal as the sensitive unit. However, it should be understood that the force transducers could have any desired construction as long as they were capable of providing an output to the controller which would indicate when at least a predetermined force is being transmitted from the upper member 498 to the lower member 494 and the soft tissue 424 and bone 426.

The connector assembly 448 includes movable members 516 and 518. The movable members 516 and 518 are connected with actuators 520 and 522. The actuators 520 and 522 are connected with the controller 456 by conductors 524 and 526.

The movable member 516 and movable member 518 extend through slots formed in the lower member 494. Thus, the lower member 494 has a cylindrical configuration and includes radially extending slots in which the movable members 516 and 518 are received. The lower (as viewed in FIG. 12) end portion of the lower member 494 is disposed in abutting engagement with the force distribution member 496 and is effective to transmit force to the force distribution member. Although the movable members 516 and 518 have been illustrated schematically in FIG. 12 as being spaced from the force distribution member 496, it should be understood that the movable members engage and slide along the force distribution member.

When the controller 456 receives an output from the transducers 478 indicating that at least a predetermined tension is present in the sections 462 and 464 of the suture 422 and receives an output from the force transducers 502 indicating that at least a predetermined force is being transmitted to the soft tissue 424 and bone 426, the controller 456 effects operation of the connector assembly 448 to interconnect the sections 462 and 464 of the suture 422. Thus, the controller 456 effects operation of the actuators 520 and 522 to press the members 516 and 518 against opposite sides of the sections 462 and 464 of the suture 422. While a predetermined clamping force is being applied against the suture sections 462 and 464 to press them against each other, the controller 456 effects operation of the connector assembly 448 to connect the sections 462 and 464 of the suture 422 to each other.

In the embodiment of the invention illustrated in FIG. 12, the sections 462 and 464 of the suture 422 are connected to each other by the application of pressure and ultrasonic vibratory energy to the sections of the suture. To enable ultrasonic vibratory energy to be transmitted to the sections of the suture, the movable member 516 functions as an anvil and the movable member 518 functions as a horn.

The movable member or horn is 518 vibrated at a rate in excess of 20 kilohertz. Although the horn 518 may be vibrated at any desired frequency within a range of 20 kilohertz to 70 kilohertz, it is believed that it may be desirable to vibrate the horn or movable member 518 at a rate which is close to or greater than 70 kilohertz. The horn 518 is vibrated for a dwell time which is sufficient to transmit enough ultrasonic vibratory energy to the sections 462 and 464 of the suture to heat a portion of the material of the sections of the suture into a transition temperature range of the material To effect a heating of the material of the suture sections 462 and 464, mechanical vibrations are transmitted from the horn or movable member 518 to an interface where the suture sections 462 and 464 are pressed against each other by the anvil 516 and horn 518. As the material of the suture sections 462 and 464 are heated into a transition temperature range, the material loses its rigidity and softens. However, the material of the sections 462 and 464 of the suture 422 do not melt and lose substantial tensile strength as the material is heated.

The heated and softened material of the sections 462 and 464 of the suture 422 are flattened from a cylindrical configuration to form thin layers which are disposed in a side-by-side relationship and have a generally plate-like configuration. As the sections 462 and 464 of the suture are pressed together and flattened, they expand in opposite directions transverse to the central axes of the suture sections.

After the suture sections have been interconnected by the connector assembly 448, a trimmer assembly 452 is operated to sever the suture sections 462 and 464 at a location between the suture tensioning assembly 438 and force application assembly 442. The trimmer assembly 452 includes cutter assemblies 540 and 542 which are connected with the controller 456 by conductors 544 and 546. A predetermined time period after the connector assembly 448 has interconnected the suture sections 462 and 464, the controller 456 effects operation of actuators in the cutter assemblies 540 and 542 to sever the suture sections.

Conclusion

In view of the foregoing description, it is apparent that the present invention relates to a method and apparatus for use in securing soft tissue 40, hard tissue 44, and/or hard and soft tissue in a patient's body. The hard tissue may be any one of the many bones in a patient's body. The soft tissue may be any one of the tissues in a patient's body other than the hard tissue.

The tissue may be secured by using a suture 36. The suture may be connected with an anchor 20. When the anchor 20 is utilized in association with the suture, the anchor may be formed of any one of many different materials including bone or other body tissue, biodegradable materials, or non-biodegradable materials. The anchor 20 may be formed of two or more different materials.

When a suture 36 is utilized to secure body tissue 40 and 44, a retainer 82 may be connected with the suture. Alternatively, sections 112 and 114 of the suture 110 may be connected with each other.

If a suture 110 is utilized to secure the body tissue, an apparatus 120, 220 or 420 may advantageously be provided to tension the suture with a predetermined force. If a retainer 244 is utilized in association with the suture, the apparatus 220 may urge the retainer toward the body tissue with a predetermined force. The retainer 244 may be connected with the suture 222 in response to detection of at least a predetermined tension in the suture and/or the transmission of a predetermined force to the body tissue 224. When the retainer 244 is to be eliminated, the sections 462, 464 of the suture 422 may be interconnected in response to detection of a predetermined tension in the suture and/or detection of the transmission of a predetermined force to the body tissue.

The anchor 22, for some uses at least, may be formed of a single piece of bone. A pointed end portion 24 of the anchor may have a surface which forms an opening in a bone or other tissue in a patient's body. The anchor 22 may be moved into the opening formed in the tissue by the pointed leading end portion of the anchor.

It should be understood that in certain situations, it may be desired to use just a suture, without an anchor, to secure the body tissue. In these situations, a retainer 82 may be connected with the suture. Alternatively, sections of the suture may be directly connected with each other. In other situations, it may be desired to use an anchor, without a suture, to secure body tissue.

Having described the invention, the following is claimed:

1. A method of securing a suture relative to a bone in a patient's body, said method comprising the steps of providing an anchor having a pointed end portion formed of bone, pressing a surface on bone forming the pointed end portion of the anchor against the bone in the patient's body, forming an opening in the bone in the patient's body under the influence of force applied against the bone in the patient's body by the surface on the bone forming the pointed end portion of the anchor, moving the anchor into the opening formed in the bone in the patient's body with the suture connected with the anchor, wherein said step of forming an opening in the bone includes enclosing the anchor with a sleeve and applying force against a trailing end portion of the anchor while the anchor is enclosed by the sleeve.

2. A method as set forth in claim 1 wherein said step of forming an opening in the bone in the patient's body includes forming an opening which extends through a compact outer layer of bone which forms a portion of the bone in the patient's body by applying force against the compact outer layer of the bone in the patient's body with the surface on bone forming the pointed end portion of the anchor and forming an opening in soft cancellous bone which forms a portion of the bone in the patient's body by applying force against the soft cancellous bone with the surface on bone forming the pointed end portion of the anchor, said step of moving the anchor into the opening formed in the bone in the patient's body includes moving the anchor through the outer layer of compact bone into the soft cancellous bone with the suture extending from the anchor through the outer layer of compact bone when the anchor is disposed in the soft cancellous bone.

3. A method as set forth in claim 2 further including the step of changing the orientation of the anchor relative to the outer layer of compact bone while the anchor is disposed in the soft cancellous bone.

4. A method as set forth in claim 3 further including the steps of tensioning the suture while the anchor is disposed in the soft cancellous in a spaced apart relationship with the outer layer of compact bone, and maintaining the anchor in a stationary relationship relative to the outer layer of compact bone with the anchor spaced apart from the outer layer of compact bone while tensioning the suture by transmitting force from the anchor to the soft cancellous bone.

5. A method as set forth in claim 3 wherein said step of changing the orientation of the anchor relative to the outer layer of compact bone is performed while the anchor is spaced apart from the outer layer of compact bone and while the anchor is engaged by only the suture and the soft cancellous bone.

6. A method as set forth in claim 3 wherein said step of changing the orientation of the anchor relative to the outer layer of compact bone includes pivoting the anchor under the influence of only force transmitted to the anchor through the suture and the soft cancellous bone.

7. A method as set forth in claim 1 further including the step of moving the suture anchor through soft body tissue, said step of pressing a surface on bone forming the pointed end portion of the anchor against the bone in the patient's body is initiated with a portion of the anchor disposed in the soft body tissue.

8. A method as set forth in claim 1 further including the step of moving the anchor through soft body tissue, and securing the soft body tissue against movement relative to the bone in the patient's body by transmitting force from the anchor to the soft body tissue through the suture after performing said step of moving the anchor into the opening formed in the bone in the patient's body.

9. A method as set forth in claim 1 wherein the anchor has first and second openings through which the suture extends and the suture has a first section which extends from the first opening in the anchor and a second section which extends from the second opening in the anchor, said step of moving the anchor into the opening formed in the bone includes moving the portion of the anchor in which the first and second openings are disposed into the bone with the first and second sections of the suture extending from the anchor to a location outside of the bone.

10. A method as set forth in claim 9 further including the step of increasing the length of one of the sections of the suture and decreasing the length of the other section of the suture while the anchor is disposed in the opening formed in the bone by tensioning the one section of the suture.

11. A method as set forth in claim 1 wherein the suture has first and second sections which extend from the anchor, said method further includes moving the anchor through soft body tissue with the first and second sections of the suture extending from the anchor, said step of moving the anchor into the opening in the bone being completed with the anchor spaced from the soft body tissue and with at least one of the first and second sections of the suture extending through the soft body tissue.

12. A method as set forth in claim 11 further including the steps of tensioning the first and second sections of the suture and gripping the first and second sections of the suture with a suture retainer while tensioning the first and second sections of the suture.

13. A method of securing a suture relative to a bone in a patient's body, said method comprising the steps of providing an anchor having a pointed end portion formed of bone and first and second sections of the suture extending from the anchor, moving the anchor through soft body tissue with the first and second sections of the suture extending from the anchor, pressing a surface on bone forming the pointed end portion of the anchor against the bone in the patient's body, forming an opening in the bone in the patient's body under the influence of force applied against the bone in the patient's body by the surface on the bone forming the pointed end portion of the anchor, moving the anchor into the opening formed in the bone in the patient's body with the suture connected with the anchor, and tensioning the first and second sections of the suture and gripping the first and second sections of the suture with a suture retainer while tensioning the first and second sections of the suture, wherein said step of moving the anchor into the opening in the bone being completed with the anchor spaced from the soft body tissue and with at least one of the first and second sections of the suture extending through the soft body tissue and wherein said step of gripping the first and second sections of the suture with the suture retainer includes pressing material of the suture retainer against the first and second sections of the suture.

14. A method of securing a suture relative to a bone in a patient's body, said method comprising the steps of providing an anchor having a pointed end portion formed of bone and first and second sections of the suture extending from the anchor, moving the anchor through soft body tissue with the first and second sections of the suture extending from the anchor, pressing a surface on bone forming the pointed end portion of the anchor against the bone in the patient's body, forming an opening in the bone in the patient's body under the influence of force applied against the bone in the patient's body by the surface on the bone forming the pointed end portion of the anchor, moving the anchor into the opening formed in the bone in the patient's body with the suture connected with the anchor, and tensioning the first and second sections of the suture and gripping the first and second sections of the suture with a suture retainer while tensioning the first and second sections of the suture, wherein said step of moving the anchor into the opening in the bone being completed with the anchor spaced from the soft body tissue and with at least one of the first and second sections of the suture extending through the soft body tissue and wherein said step of gripping the first and second sections of the suture with the suture retainer includes applying force against the suture retainer and cold flowing material of the suture retainer under the influence of the force applied against the suture retainer.

15. A method of securing a suture relative to a bone in a patient's body, said method comprising the steps of providing an anchor having a pointed end portion formed of bone and first and second sections of the suture extending from the anchor, moving the anchor through soft body tissue with the first and second sections of the suture extending from the anchor, pressing a surface on bone forming the pointed end portion of the anchor against the bone in the patient's body, forming an opening in the bone in the patient's body under the influence of force applied against the bone in the patient's body by the surface on the bone forming the pointed end portion of the anchor, moving the anchor into the opening formed in the bone in the patient's body with the suture connected with the anchor, and tensioning the first and second sections of the suture and gripping the first and second sections of the suture with a suture retainer while tensioning the first and second sections of the suture, wherein said step of moving the anchor into the opening in the bone being completed with the anchor spaced from the soft body tissue and with at least one of the first and second sections of the suture extending through the soft body tissue and wherein the step of gripping the first and second sections of the suture with the suture retainer includes transmitting ultrasonic vibratory energy to the suture retainer.

16. A method of securing a suture relative to a bone in a patient's body, said method comprising the steps of providing an anchor having a pointed end portion formed of bone and first and second sections of the suture extending from the anchor, moving the anchor through soft body tissue with the first and second sections of the suture extending from the anchor, pressing a surface on bone forming the pointed end portion of the anchor against the bone in the patient's body, forming an opening in the bone in the patient's body under the influence of force applied against the bone in the patient's body by the surface on the bone forming the pointed end portion of the anchor, moving the anchor into the opening formed in the bone in the patient's body with the suture connected with the anchor, tensioning the first and second sections of the suture, and bonding the first and second sections of the suture together, wherein said step of moving the anchor into the opening in the bone being completed with the anchor spaced from the soft body tissue and with at least one of the first and second sections of the suture extending through the soft body tissue.

17. A method as set forth in claim 16 wherein said step of bonding the first and second sections of the suture together includes transmitting ultrasonic vibratory energy to at least one of the first and second sections of the suture and pressing the first and second sections of the suture against each other.

18. A method of securing a suture relative to a bone in a patient's body, said method comprising the steps of providing an anchor having a pointed end portion formed of bone, pressing a surface on bone forming the pointed end portion of the anchor against the bone in the patient's body, forming an opening in the bone in the patient's body under the influence of force applied against the bone in the patient's body by the surface on the bone forming the pointed end portion of the anchor, and moving the anchor into the opening formed in the bone in the patient's body with the suture connected with the anchor, wherein the method further includes the steps of securing a portion of body tissue disposed in the patient's body against movement relative to the bone in the patient's body, said step of securing body tissue includes tensioning the suture with the anchor disposed in the opening formed in the bone in the patient's body, positioning a suture retainer relative to the suture, and securing the suture retainer against movement relative to the suture while continuing to tension the suture.

19. A method as set forth in claim 18 further including the step of pressing the body tissue against the bone in the patient's body under the influence of force transmitted through the suture between the suture retainer and the anchor while the anchor is disposed in the opening formed in the bone in the patient's body.

20. A method as set forth in claim 19 wherein said step of securing the suture retainer against movement relative to the suture includes gripping the suture with the suture retainer.

21. A method as set forth in claim 19 wherein said step of securing the suture retainer against movement relative to the suture includes pressing material of the suture retainer against the suture by cold flowing material of the suture retainer.

22. A method as set forth in claim 19 wherein said step of securing the suture retainer against movement relative to the suture includes deforming material of the suture retainer without significant deformation of the suture.

23. A method as set forth in claim 19 wherein said step of securing the suture retainer against movement relative to the suture includes heating the suture retainer by transmitting ultrasonic vibratory energy to the suture retainer.

24. A method of securing a suture relative to a bone in a patient's body, said method comprising the steps of providing an anchor having a pointed end portion formed of bone, pressing a surface on bone forming the pointed end portion of the anchor against the bone in the patient's body, forming an opening in the bone in the patient's body under the influence of force applied against the bone in the patient's body by the surface on the bone forming the pointed end portion of the anchor, moving the anchor into the opening formed in the bone in the patient's body with the suture connected with the anchor, positioning a suture retainer relative to the suture, increasing the tension in the suture to a predetermined tension, and transmitting ultrasonic vibratory energy to the suture retainer in response to an increase in the tension in the suture to a predetermined tension.

25. A method of securing a suture relative to a bone in a patient's body, said method comprising the steps of providing an anchor having a pointed end portion formed of bone, pressing a surface on bone forming the pointed end portion of the anchor against the bone in the patient's body, forming an initial opening in the bone in the patient's body, forming an opening in the bone in the patient's body under the influence of force applied against the bone in the patient's body by the surface on the bone forming the pointed end portion of the anchor, moving the anchor into the opening formed in the bone in the patient's body with the suture connected with the anchor, wherein said step of forming an opening in the bone includes enlarging the initial opening in the bone in the patient's body.

26. A method of securing tissue to a bone in a patient's body, said method comprising the steps of providing an anchor having a pointed end portion, pressing a surface on the pointed end portion of the anchor against the tissue, forming an opening in the tissue under the influence of force applied against the tissue by the surface on the pointed end portion of the anchor, moving the anchor into the opening formed in the tissue, pressing the surface on the pointed end portion of the anchor against the bone in the patient's body, forming an opening in the bone in the patient's body under the influence of force applied against the bone in the patient's body by the surface on the pointed end portion of the anchor, moving the anchor into the opening formed in the bone in the patient's body, and securing the tissue against movement relative to the bone, said step of securing tissue includes tensioning a suture connected with the anchor and partially disposed in the opening formed in the bone in the patient's body and with a portion of the suture extending from the bone in the patient's body into engagement with the tissue, positioning a suture retainer relative to the suture, and securing the suture retainer against movement relative to the suture while continuing to tension the suture.

27. A method as set forth in claim 26 wherein said step of forming an opening in the bone in the patient's body includes forming an opening which extends through a compact outer layer of bone which forms a portion of the bone in the patient's body by applying force against the compact outer layer of the bone in the patient's body with the surface on the pointed end portion of the anchor and forming an opening in soft cancellous bone which forms a portion of the bone in the patient's body by applying force against the soft cancellous bone with the surface on the pointed end portion of the anchor, said step of moving the anchor into the opening formed in the bone in the patient's body includes moving the anchor through the outer layer of compact bone into the soft cancellous bone.

28. A method as set forth in claim 27 further including the step of changing the orientation of the anchor relative to the outer layer of compact bone while the anchor is disposed in the soft cancellous bone.

29. A method as set forth in claim 28 wherein the suture is tensioned while the suture extends through the tissue and while the anchor is disposed in the soft cancellous bone in a spaced apart relationship with the outer layer of compact bone, and the method further includes the steps of maintaining the anchor in a stationary relationship relative to the outer layer of compact bone while the anchor is spaced apart from the outer layer of compact bone while tensioning the suture by transmitting force from the anchor to the soft cancellous bone and, pressing the tissue against the outer layer of compact bone while suture extends through the tissue and is being tensioned.

30. A method as set forth in claim 28 wherein the suture is tensioned while the suture extends through the tissue into the bone, said step of changing the orientation of the anchor relative to the outer layer of compact bone is performed while the anchor is spaced apart from the outer layer of compact bone and while the anchor is engaged by only the suture and the soft cancellous bone, said step of changing the orientation of the anchor relative to the outer layer of compact bone includes transmitting force from the suture to the anchor while tensioning the suture.

31. A method as set forth in claim 26 wherein the anchor has first and second openings through which the suture extends and the suture has a first section which extends from the first opening in the anchor and a second section which extends from the second opening in the anchor, said step of moving the anchor into the opening formed in the bone includes moving the portion of the anchor in which the first and second openings are disposed into the bone with the first and second sections of the suture extending from the anchor through the tissue.

32. A method as set forth in claim 31 further including the step of increasing the length of one of the sections of the suture and decreasing the length of the other section of the suture while the anchor is disposed in the opening formed in the bone and while the first and second sections of the suture extend through the tissue by tensioning the one section of the suture.

33. A method a set forth in claim 26 wherein the suture connected with the anchor has first and second sections which extend from the anchor through the tissue during at least a portion of the movement of the anchor into the opening formed in the bone in the patient's body, said method further includes moving the first section of the suture out of tissue while the second section of the suture continues to extend through the tissue, and interconnecting the first and second sections of the suture while only the second section of the suture extends through the tissue and while the first and second section of the suture are connected with the anchor.

34. A method as set forth in claim 33 further including the step of tensioning the first and second sections of the suture and gripping the first and second sections of the suture with a suture retainer while tensioning the first and second sections of the suture with only the second section of the suture extending through the tissue.

35. A method as set forth in claim 34 further including the step of tensioning the first and second sections of the suture and bonding the first and second sections of the suture together with only the second section of the suture extending through the tissue.

36. A method as set forth in claim 35 wherein said step of bonding the first and second sections of the suture together includes transmitting ultrasonic vibratory energy to at least one of the first and second sections of the suture and pressing the first and second sections of the suture against each other.

37. A method as set forth in claim 26 wherein said step of positioning the suture retainer relative to the tissue is performed with a portion of the suture extending through the tissue, said method further includes pressing the tissue against the bone under the influence of force transmitted through the suture between the suture retainer and the anchor while the anchor is disposed in the opening formed in the bone in the patient's body and with a portion of the suture extending through the tissue.

38. A method as set forth in claim 37 wherein said step of securing the suture retainer against movement relative to the suture includes gripping the suture with the suture retainer.

39. A method as set forth in claim 37 wherein said step of securing the suture retainer against movement relative to the suture includes pressing material of the suture retainer against the suture by cold flowing material of the suture retainer.

40. A method as set forth in claim 37 wherein said step of securing the suture retainer against movement relative to the suture includes deforming material of the suture retainer without significant deformation of the suture.

41. A method as set forth in claim 37 wherein said step of securing the suture retainer against movement relative to the suture includes heating the suture retainer by transmitting ultrasonic vibratory energy to the suture retainer.

42. A method of securing tissue to a bone in a patient's body, said method comprising the steps of providing an anchor having a pointed end portion, pressing a surface on the pointed end portion of the anchor against the tissue, forming an opening in the tissue under the influence of force applied against the tissue by the surface on the pointed end portion of the anchor, moving the anchor into the opening formed in the tissue, pressing the surface on the pointed end portion of the anchor against the bone in the patient's body, forming an opening in the bone in the patient's body under the influence of force applied against the bone in the patient's body by the surface on the pointed end portion of the anchor, moving the anchor into the opening formed in the bone in the patient's body, positioning a suture retainer relative to a suture connected with the anchor, increasing tension in the suture to a predetermined tension, and transmitting ultrasonic vibratory energy to the suture retainer in response to an increase in the tension in the suture to a predetermined tension.

43. A method of securing tissue to a bone in a patient's body, said method comprising the steps of providing an anchor having a pointed end portion, pressing a surface on the pointed end portion of the anchor against the tissue, forming an initial opening in the bone in the patient's body, forming an opening in the tissue under the influence of force applied against the tissue by the surface on the pointed end portion of the anchor, moving the anchor into the opening formed in the tissue, pressing the surface on the pointed end portion of the anchor against the bone in the patient's body, forming an opening in the bone in the patient's body under the influence of force applied against the bone in the patient's body by the surface on the pointed end portion of the anchor, and moving the anchor into the opening formed in the bone in the patient's body, wherein said step of forming an opening in the bone in the patient's body under the influence of force applied against the bone in the patient's body by the surface on the pointed end portion of the anchor includes enlarging the initial opening in the bone in the patient's body.

44. A method of securing tissue to a bone in a patient's body, said method comprising the steps of providing an anchor having a pointed end portion, pressing a surface on the pointed end portion of the anchor against the tissue, forming an opening in the tissue under the influence of force applied against the tissue by the surface on the pointed end portion of the anchor, moving the anchor into the opening formed in the tissue, pressing the surface on the pointed end portion of the anchor against the bone in the patient's body, forming an opening in the bone in the patient's body under the influence of force applied against the bone in the patient's body by the surface on the pointed end portion of the anchor, moving the anchor into the opening formed in the bone in the patient's body, wherein the anchor is formed by a single piece of bone, said step of forming an opening in the bone in the patient's body includes enclosing the anchor with a sleeve and applying force against a trailing end portion of the anchor while the anchor is enclosed by the sleeve.

45. A method of securing first tissue in a patient's body to second tissue in the patient's body, said method comprising the steps of positioning an anchor relative to the second tissue with a suture connected with the anchor and extending from the second tissue, positioning a retainer relative to the suture, transmitting force from the retainer to the first tissue to urge the first tissue toward the second tissue, tensioning the suture, said step of tensioning the suture includes detecting when at least a predetermined tension is present in the suture, and connecting the retainer with the suture in response to detection of at least the predetermined tension in the suture.

46. A method as set forth in claim 45 wherein the anchor has a pointed end portion formed of bone and the second tissue is bone disposed in a patient's body, said step of positioning the anchor relative to the second tissue includes pressing a surface on the bone forming the pointed end portion of the anchor against the bone in the patient's body, forming an opening in the bone in the patient's body under the influence of force applied against the bone in the patient's body by the surface on the bone forming the pointed end portion of the anchor, and moving the anchor into the opening formed in the bone in the patient's body with the suture connected with the anchor.

47. A method as set forth in claim 45 wherein said step of connecting the retainer with the suture in response to detection of the predetermined tension in the suture includes transmitting ultrasonic vibratory energy to the retainer in response to detection of the predetermined tension in the suture.

48. A method as set forth in claim 47 wherein said step of transmitting ultrasonic vibratory energy to the retainer includes heating material of the retainer under the influence of the ultrasonic vibratory energy.

49. A method as set forth in claim 48 wherein said step of connecting the retainer with the suture includes pressing heated material of the retainer against the suture and forming a bond between material of the retainer and the suture.

50. A method as set forth in claim 45 wherein said step of tensioning the suture includes holding the suture at a first location offset from the retainer in a direction away from the first tissue, said step of connecting the retainer with the suture includes bonding material of the retainer to the suture at a second location which is disposed closer to the first tissue than the first location, said method further includes severing the suture at a third location which is disposed between the first and second locations after performing said step of connecting the retainer with the suture.

51. A method as set forth in claim 45 wherein said step of connecting the retainer with the suture includes plastically deforming material of the retainer and pressing material of the retainer against the suture.

52. A method as set forth in claim 45 further including the step of positioning the suture relative to the first tissue with a portion of the suture extending through the first tissue, said step of positioning the suture relative to the first tissue includes moving the anchor through the first tissue with the suture connected to the anchor, said step of positioning the retainer relative to the suture includes moving the retainer to a desired position relative to the suture, said method further includes transmitting a predetermined force from the retainer to the first tissue, said step of connecting the retainer with the suture being performed while the predetermined force is transmitted from the retainer to the first tissue and while the predetermined tension is maintained in the suture.

53. A method as set forth in claim 52 wherein said step of connecting the retainer with the suture includes transmitting ultrasonic vibratory energy to the retainer.

54. A method as set forth in claim 52 wherein said step of connecting the retainer with the suture includes heating material of the retainer and plastically deforming the heated material of the retainer.

55. A method as set forth in claim 52 wherein said step of connecting the retainer with the suture includes applying force against the retainer and cold flowing material of the retainer under the influence of the force applied against the retainer.

56. A method as set forth in claim 45 wherein the suture includes first and second sections which extend from the anchor, said method further includes positioning the first and second sections of the suture relative to the first tissue, said step of positioning the retainer relative to the suture includes moving the retainer to a desired position relative to the first tissue and the suture, said step of tensioning the suture includes tensioning the first and second sections of the suture with a predetermined tension, said method further includes transmitting a predetermined force from the retainer to the first tissue, said step of connecting the retainer with the suture includes connecting the retainer with the first and second sections of the suture while tensioning the first and second sections of the suture with the predetermined tension and while transmitting the predetermined force from the retainer to the first tissue.

57. A method as set forth in claim 56 wherein said step of connecting the retainer with the suture includes transmitting ultrasonic vibratory energy to the retainer.

58. A method as set forth in claim 56 wherein said step of connecting the retainer with the suture includes heating material of the retainer and plastically deforming the heated material of the retainer.

59. A method as set forth in claim 56 wherein said step of connecting the retainer with the suture includes applying force against the retainer and cold flowing material of the retainer under the influence of the force applied against the retainer.

60. A method of securing first tissue in a patient's body to second tissue in the patient's body, said method comprising the steps of positioning an anchor relative to the second tissue with a suture connected with the anchor and extending from the second tissue, positioning a retainer relative to the suture, transmitting force from the retainer to the first tissue to urge the first tissue toward the second tissue, said step of transmitting force from the retainer to the first tissue includes detecting when at least a predetermined force is transmitted to the first tissue, tensioning the suture, and connecting the retainer with the suture in response to detection of transmission of at least the predetermined force to the first tissue.

61. A method as set forth in claim 60 wherein the anchor has a pointed end portion formed of bone and the second tissue is bone disposed in a patient's body, said step of positioning the anchor relative to the second tissue includes pressing a surface on the bone forming the pointed end portion of the anchor against the bone in the patient's body, forming an opening in the bone in the patient's body under the influence of force applied against the bone in the patient's body by the surface on the bone forming the pointed end portion of the anchor, and moving the anchor into the opening formed in the bone in the patient's body with the suture connected with the anchor.

62. A method as set forth in claim 60 wherein said step of connecting the retainer with the suture in response to detection of transmission of the predetermined force to the first tissue includes transmitting ultrasonic vibratory energy to the retainer in response to detection of transmission of the predetermined force to the first tissue.

63. A method as set forth in claim 62 wherein said step of transmitting ultrasonic vibratory energy to the retainer includes heating material of the retainer under the influence of the ultrasonic vibratory energy.

64. A method as set forth in claim 63 wherein said step of connecting the retainer with the suture includes pressing heated material of the retainer against the suture and forming a bond between material of the retainer and the suture.

65. A method as set forth in claim 60 wherein said step of tensioning the suture includes holding the suture at a first location offset from the retainer in a direction away from the first tissue, said step of connecting the retainer with the suture includes bonding material of the retainer to the suture at a second location which is disposed closer to the first tissue than the first location, said method further includes severing the suture at a third location which is disposed between the first and second locations after performing said step of connecting the retainer with the suture.

66. A method as set forth in claim 60 wherein said step of connecting the retainer with the suture includes plastically deforming material of the retainer and pressing material of the retainer against the suture.

67. A method as set forth in claim 60 further including the step of positioning the suture relative to the first tissue with a portion of the suture extending through the first tissue, said step of positioning the suture relative to the first tissue includes moving the anchor through the first tissue with the suture connected to the anchor, said step of positioning the retainer relative to the suture includes moving the retainer to a desired position relative to the suture, said method further includes tensioning the suture with a predetermined tension, said step of connecting the retainer with the suture being performed while the predetermined force is transmitted from the retainer to the first tissue and while the predetermined tension is maintained in the suture.

68. A method as set forth in claim 67 wherein said step of connecting the retainer with the suture includes transmitting ultrasonic vibratory energy to the retainer.

69. A method as set forth in claim 67 wherein said step of connecting the retainer with the suture includes heating material of the retainer and plastically deforming the heated material of the retainer.

70. A method as set forth in claim 60 wherein said step of connecting the retainer with the suture includes applying force against the retainer and cold flowing material of the retainer under the influence of the force applied against the retainer.

71. A method as set forth in claim 60 wherein the suture includes first and second sections which extend from the anchor, said method further includes positioning the first and second sections of the suture relative to the first tissue, said step of positioning the retainer relative to the suture includes moving the retainer to a desired position relative to the first tissue and the suture, said step of tensioning the suture includes tensioning the first and second sections of the suture with a predetermined tension, said step of connecting the retainer with the suture includes connecting the retainer with the first and second sections of the suture while tensioning the first and second sections of the suture with the predetermined tension and while transmitting the predetermined force from the retainer to the first tissue.

72. A method as set forth in claim 71 wherein said step of connecting the retainer with the suture includes transmitting ultrasonic vibratory energy to the retainer.

73. A method as set forth in claim 71 wherein said step of connecting the retainer with the suture includes heating material of the retainer and plastically deforming the heated material of the retainer.

74. A method as set forth in claim 71 wherein said step of connecting the retainer with the suture includes applying force against the retainer and cold flowing material of the retainer under the influence of the force applied against the retainer.

75. A method of securing first tissue in a patient's body to second tissue in the patient's body, said method comprising the steps of positioning an anchor relative to the second tissue with a suture connected with the anchor and extending from the second tissue, positioning a retainer relative to the suture, transmitting force from the retainer to the first tissue to urge the first tissue toward the second tissue, said step of transmitting force from the retainer to the first tissue includes detecting when at least a predetermined force is transmitted to the first tissue, tensioning the suture, said step of tensioning the suture includes detecting when at least a predetermined tension is present in the suture, and connecting the retainer with the suture in response to detection of both the predetermined tension in the suture and the transmission of the predetermined force to the first tissue.

76. A method as set forth in claim 75 wherein the anchor has a pointed end portion formed of bone and the second tissue is bone disposed in a patient's body, said step of positioning the anchor relative to the second tissue includes pressing a surface on the bone forming the pointed end portion of the anchor against the bone in the patient's body, forming an opening in the bone in the patient's body under the influence of force applied against the bone in the patient's body by the surface on the bone forming the pointed end portion of the anchor, and moving the anchor into the opening formed in the bone in the patient's body with the suture connected with the anchor.

77. A method as set forth in claim 75 wherein said step of connecting the retainer with the suture in response to detection of the predetermined tension in the suture and the transmission of the predetermined force to the first tissue includes transmitting ultrasonic vibratory energy to the retainer in response to detection of the predetermined tension in the suture and the transmission of the predetermined force to the first tissue.

78. A method as set forth in claim 77 wherein said step of transmitting ultrasonic vibratory energy to the retainer includes heating material of the retainer under the influence of the ultrasonic vibratory energy.

79. A method as set forth in claim 78 wherein said step of connecting the retainer with the suture includes pressing heated material of the retainer against the suture and forming a bond between material of the retainer and the suture.

80. A method as set forth in claim 79 wherein said step of tensioning the suture includes holding the suture at a first location offset from the retainer in a direction away from the first tissue, said step of connecting the retainer with the suture includes bonding material of the retainer to the suture at a second location which is disposed closer to the first tissue than the first location, said method further includes severing the suture at a third location which is disposed between the first and second locations after performing said step of connecting the retainer with the suture.

81. A method as set forth in claim 75 wherein said step of connecting the retainer with the suture includes plastically deforming material of the retainer and pressing material of the retainer against the suture.

82. A method as set forth in claim 75 further including the step of positioning the suture relative to the first tissue with a portion of the suture extending through the first tissue, said step of positioning the suture relative to the first tissue includes moving the anchor through the first tissue with the suture connected to the anchor.

83. A method as set forth in claim 82 wherein said step of connecting the retainer with the suture includes transmitting ultrasonic vibratory energy to the retainer.

84. A method as set forth in claim 82 wherein said step of connecting the retainer with the suture includes heating material of the retainer and plastically deforming the heated material of the retainer.

85. A method as set forth in claim 82 wherein said step of connecting the retainer with the suture includes applying force against the retainer and cold flowing material of the retainer under the influence of the force applied against the retainer.

86. A method as set forth in claim 75 wherein the suture includes first and second sections which extend from the anchor, said method further includes positioning the first and second sections of the suture relative to the first tissue, said step of positioning the retainer relative to the suture includes moving the retainer to a desired position relative to the first tissue and the suture, said step of tensioning the suture includes tensioning the first and second sections of the suture with a predetermined tension, said step of connecting the retainer with the suture includes connecting the retainer with the first and second sections of the suture while tensioning the first and second sections of the suture with the predetermined tension and while transmitting the predetermined force from the retainer to the first tissue.

87. A method as set forth in claim 86 wherein said step of connecting the retainer with the suture includes transmitting ultrasonic vibratory energy to the retainer.

88. A method as set forth in claim 86 wherein said step of connecting the retainer with the suture includes heating material of the retainer and plastically deforming the heated material of the retainer.

89. A method as set forth in claim 86 wherein said step of connecting the retainer with the suture includes applying force against the retainer and cold flowing material of the retainer under the influence of the force applied against the retainer.

90. A method of securing first tissue in a patient's body to second tissue in the patient's body, said method comprising the steps of positioning an anchor relative to the second tissue with first and second sections of a suture connected with the anchor and extending from the second tissue, positioning the first and second sections of the suture relative to the first tissue, tensioning the first and second sections of the suture, and connecting the first and second sections of the suture together, said step of connecting the first and second sections of the suture together includes transmitting ultrasonic vibratory energy to at least one of the first and second sections of the suture and pressing the first section of the suture against the second section of the suture.

91. A method as set forth in claim 90 wherein the anchor has a pointed end portion formed of bone and the second tissue is bone disposed in a patient's body, said step of positioning the anchor relative to the second tissue includes pressing a surface on the bone forming the pointed end portion of the anchor against the bone in the patient's body, forming an opening in the bone in the patient's body under the influence of force applied against the bone in the patient's body by the surface on the bone forming the pointed end portion of the anchor, and moving the anchor into the opening formed in the bone in the patient's body with the suture connected with the anchor.

92. A method as set forth in claim 90 wherein said step of tensioning the suture includes detecting when a predetermined tension is present in the suture, said step of connecting the first and second sections of the suture together being performed in response to detection of the predetermined tension in the suture.

93. A method as set forth in claim 90 wherein said step of transmitting ultrasonic vibratory energy to at least one of the first and second sections of the suture includes heating at least the one section of the suture under the influence of the ultrasonic vibratory energy.

94. A method as set forth in claim 93 wherein said step of pressing the first section of the suture against the second section of the suture includes pressing the heated material of the one section of the suture and the other section of the suture together and forming a bond between the first and second sections of the suture.

95. A method as set forth in claim 90 wherein said step of tensioning the suture includes holding the suture at a first location offset from the retainer in a direction away from the first tissue, said step of connecting the first and second sections of the suture together includes bonding material of the first and second sections of the suture together at a second location which is disposed closer to the first tissue than the first location, said method further includes severing the first and second sections of the suture at a third location which is disposed between the first and second locations after performing said step of connecting the first and second sections of the suture together.

96. A method as set forth in claim 90 wherein said step of connecting the first and second sections of the suture together includes plastically deforming at least the material of the one section of the suture.

97. A method as set forth in claim 90 wherein said step of positioning the suture relative to the first tissue includes moving the anchor through the first tissue with the suture connected to the anchor.

98. A method as set forth in claim 90 further including the step of transmitting a predetermined force from the first and second sections of the suture to the first tissue, said step of connecting the first and second sections of the suture together being performed in response to detection of transmission of the predetermined force from the first and second sections of the suture to the first body tissue.

99. A method of securing a suture relative to body tissue, said method comprises the steps of positioning the suture relative to the body tissue, connecting the suture to a first member, establishing at least a predetermined tension in the suture by urging the first member in a direction away from the body tissue, positioning a retainer relative to the suture, establishing the transmission of at least a predetermined force from the retainer to the body tissue by urging the retainer toward the body tissue, and connecting the retainer with the suture while at least the predetermined tension is present in the suture and while at least the predetermined force is being transmitted from the retainer to the body tissue, said step of connecting the retainer with the suture includes transmitting ultrasonic vibratory energy to the retainer.

100. A method as set forth in claim 99 wherein said step of positioning the suture relative to the body tissue includes moving an anchor connected with the suture into a bone in the patient's body.

101. A method as set forth in claim 100 wherein said step of establishing at least a predetermined tension in the suture by urging the first member in a direction away from the body tissue includes transmitting force from the first member to the anchor through the suture.

102. A method as set forth in claim 100 wherein said step of establishing the transmission of at least a predetermined force from the retainer to the body tissue by urging the retainer toward the body tissue includes pressing body tissue against the bone in the patient's body under the influence of force transmitted from the retainer to the body tissue.

103. A method as set forth in claim 100 wherein the anchor has a pointed end portion, said step of moving the anchor connected with the suture into the bone in the patient's body includes forming an opening in the bone in the patient's body under the influence of force applied against the bone in the patient's body by the pointed end portion of the anchor.

104. A method as set forth in claim 100 wherein said step of positioning the suture relative to body tissue further includes moving the anchor connected with the suture through body tissue contemporaneously with performance of said step of moving the anchor into the bone in the patient's body.

105. A method as set forth in claim 100 further including the step of severing the suture at a location disposed between the first member and the retainer while the suture is tensioned by urging the first member in a direction away from the body tissue and after performance of said step of connecting the retainer with the suture.

106. A method as set forth in claim 99 further including the steps of detecting when the predetermined tension is established in the suture and detecting when the predetermined force is transmitted from the retainer to the body tissue, said step of connecting the retainer with the suture being performed in response to detection that the predetermined tension has been established in the suture and detection that the predetermined force is being transmitted from the retainer to the body tissue.

107. A method of securing a suture relative to body tissue, said method comprises the steps of positioning the suture relative to body tissue, connecting first and second sections of the suture to a first member, establishing at least a predetermined tension in the first and second sections of the suture by urging the first member in a direction away from the body tissue, establishing the transmission of at least a predetermined force from a second member to the body tissue by urging the second member in a direction toward the body tissue, and connecting the first and second sections of the suture together while at least the predetermined tension is present in the suture and while at least the predetermined force is being transmitted from the second member to the body tissue, said step of connecting the first and second sections of the suture together includes transmitting ultrasonic vibratory energy to at least one of the sections of the suture and pressing the first section of the suture against the second section of the suture.

108. A method as set forth in claim 107 wherein said step of positioning the suture relative to the body tissue includes moving an anchor connected with the suture into a bone in the patient's body.

109. A method as set forth in claim 108 wherein said step of establishing at least a predetermined tension in the suture by urging the first member in a direction away from the body tissue includes transmitting force from the first member to the anchor through the suture.

110. A method as set forth in claim 108 wherein said step of establishing the transmission of at least a predetermined force from the second member to the body tissue by urging the second member toward the body tissue includes pressing body tissue against the bone in the patient's body under the influence of force transmitted from the second member to the body tissue.

111. A method as set forth in claim 108 wherein the anchor has a pointed end portion, said step of moving the anchor connected with the suture into the bone in the patient's body includes forming an opening in the bone in the patient's body under the influence of force applied against the bone in the patient's body by the pointed end portion of the anchor.

112. A method as set forth in claim 108 wherein said step of positioning the suture relative to body tissue further includes moving the anchor connected with the suture through body tissue contemporaneously with performance of said step of moving the anchor into the bone in the patient's body.

113. A method as set forth in claim 107 further including the step of severing the suture at a location disposed between the first member and the second member while the suture is tensioned by urging the first member in a direction away from the body tissue and after performance of said step of connecting the first and second sections of the suture together.

114. A method as set forth in claim 107 further including the steps of detecting when the predetermined tension is established in the suture and detecting when the predetermined force is transmitted from the second member to the body tissue, said step of connecting the first and second sections of the suture together being performed in response to detection that the predetermined tension has been established in the suture and detection that the predetermined force is being transmitted from the second member to the body tissue.

115. An apparatus for use in securing a suture relative to body tissue, said apparatus comprising means for tensioning the suture with at least a predetermined tension, means for applying at least a predetermined force to a retainer to urge the retainer toward the body tissue, means for detecting when at least the predetermined tension is present in the suture, and means for connecting the retainer with the suture, said means for connecting the retainer with the suture being operable to connect the retainer with the suture in response to detection that at least the predetermined tension is present in the suture.

116. An apparatus as set forth in claim 115 further including means for detecting when at least the predetermined force is applied to the retainer, said means for connecting the retainer with the suture being operable to connect the retainer with the suture in response to detection that the predetermined tension is present in the suture and that the predetermined force is being applied to the retainer.

117. An apparatus as set forth in claim 115 wherein said means for connecting the retainer with the suture is operable to apply ultrasonic vibratory energy to the retainer.

118. An apparatus as set forth in claim 115 further including means for severing the suture.

119. An apparatus for use in securing a suture relative to body tissue, said apparatus comprising means for tensioning the suture with at least a predetermined tension, means for applying a predetermined force to a retainer to urge the retainer toward the body tissue, means for detecting when at least a predetermined force is applied to the retainer, and means for connecting the retainer with the suture, said means for connecting the retainer with the suture being operable to connect the retainer with the suture in response to detection that at least the predetermined force is being applied to the retainer.

120. An apparatus as set forth in claim 119 further including means for detecting when at least a predetermined tension is present in the suture.

121. An apparatus as set forth in claim 119 wherein said means for connecting the retainer with the suture is operable to apply ultrasonic vibratory energy to the retainer.

122. An apparatus as set forth in claim 119 further including means for severing the suture.

123. An apparatus for use in securing first and second sections of a suture relative to body tissue, said apparatus comprising means for tensioning the first and second sections of the suture with at least a predetermined tension, means for applying at least a predetermined force which is transmitted to the body tissue and is effective to urge the body tissue in a direction away from said means for tensioning the first and second sections of the suture with at least the predetermined tension, means for detecting when at least the predetermined tension is present in the first and second sections of the suture, and means for interconnecting the first and second sections of the suture, said means for interconnecting the first and second sections of the suture being operable to interconnect the first and second sections of the suture in response to detection that at least the predetermined tension is present in the first and second sections of the suture.

124. A method as set forth in claim 123 further including means for detecting when at least the predetermined force is transmitted to the body tissue, said means for interconnecting the first and second sections of the suture being operable to interconnect the first and second sections of the suture in response to detection that the predetermined tension is present in the first and second sections of the suture and that at least the predetermined force is being transmitted to the body tissue.

125. An apparatus as set forth in claim 123 wherein said means for interconnecting the first and second sections of the suture includes means for pressing the first and second sections of the suture against each other and for bonding the first and second sections of the suture together.

126. An apparatus as set forth in claim 123 wherein said means for interconnecting the first and second sections of the suture includes means for applying ultrasonic vibratory energy to at least one of the sections of the suture and for pressing the first and second sections of the suture together.

127. An apparatus as set forth in claim 123 further including means for severing the first and second sections of the suture.

128. An apparatus for use in securing first and second sections of a suture relative to body tissue, said apparatus comprising means for tensioning the first and second sections of the suture with at least a predetermined tension, means for applying at least a predetermined force which is transmitted to the body tissue and is effective to urge the body tissue in a direction away from said means for tensioning the first and second sections of the suture with at least a predetermined tension, means for detecting when at least the predetermined force is transmitted to the body tissue, and means for interconnecting the first and second sections of the suture, said means for interconnecting the first and second sections of the suture being operable to interconnect the first and second sections of the suture in response to detection that at least the predetermined force is being transmitted to the body tissue.

129. An apparatus as set forth in claim 128 further including means for detecting when at least a predetermined tension is present in the first and second sections of the suture.

130. An apparatus as set forth in claim 128 wherein said means for interconnecting the first and second sections of the suture includes means for pressing the first and second sections of the suture against each other and for bonding the first and second sections of the suture together.

131. An apparatus as set forth in claim 128 wherein said means for interconnecting the first and second sections of the suture includes means for applying ultrasonic vibratory energy to at least one of the sections of the suture and for pressing the first and second sections of the suture together.

132. An apparatus as set forth in claim 128 further including means for severing the first and second sections of the suture.

133. An apparatus for use in securing a suture relative to body tissue, said apparatus comprising a base, a first member connected with said base and connectable with the suture, said first member being urged in a direction toward the body tissue under the influence of tension force transmitted to said first member through the suture, a second member connected with said base and engageable with a retainer which is disposed adjacent to the suture, said second member being effective to transmit force to the retainer to urge the retainer toward the body tissue, and a connector assembly which is connected with said base and is operable to connect the retainer with the suture upon application of a predetermined force to at least one of said first and second members.

134. An apparatus as set forth in claim 133 wherein said connector assembly includes a vibration applicator member which transmits ultrasonic vibratory energy to the retainer to heat material of the retainer in response to application of the predetermined force to at least one of said first and second members.

135. An apparatus as set forth in claim 133 wherein said connector assembly includes clamp members and an actuator which presses said clamp members against opposite sides of the retainer to deform material of the retainer.

136. An apparatus as set forth in claim 133 further including a solid state device to which force is transmitted from one of said first and second members, said solid state device being effective to provide an output signal which is indicative of transmission of a predetermined force to the one of said first and second members, said connector assembly being operable to connect the retainer with the suture when the output signal from said solid state device indicates transmission of the predetermined force to the one of said first and second members.

137. An apparatus as set forth in claim 133 further including a cutter assembly connected with said base and operable to cut the suture at a location disposed between said first and second members.

138. An apparatus for use in securing a suture relative to body tissue, said apparatus comprising a base, a first member connected with said base and connectable with the suture, said first member being urged in a direction toward the body tissue under the influence of tension force transmitted to the first member through first and second sections of the suture, a second member connected with said base, said second member being urged toward said first member under the influence of force transmitted between said second member and the body tissue, and a connector assembly which is connected with said base and is operable to connect the first and second sections of the suture together upon application of a predetermined force to at least one of said first and second members.

139. An apparatus as set forth in claim 138 wherein said connector assembly includes a vibration applicator member which transmits ultrasonic vibratory energy to at least one of the first and second sections of the suture to heat at least the one section of the suture, said connector assembly being operable to press the first section of the suture against the second section of the suture during the application of ultrasonic vibratory energy to at least the one section of the suture.

140. An apparatus as set forth in claim 138 wherein said connector assembly is operable to bond said first and second sections of the suture together.

141. An apparatus as set forth in claim 138 wherein said actuator assembly includes a plurality of clamp members and an actuator which presses said clamp members against the first and second sections of the suture to deform material of the suture and interconnect the first and second sections of the suture.

142. An apparatus as set forth in claim 138 wherein at least one of said clamp members is effective to apply ultrasonic vibratory energy to at least one of the sections of the suture.

143. An apparatus as set forth in claim 138 further including a solid state device to which force is transmitted from one of said first and second members, said solid state device being effective to provide an output signal which is indicative of transmission of a predetermined force to the one of the first and second members, said connector assembly being operable to connect the first and second sections of the suture together when the output from said solid state device indicates transmission of the predetermined force to the one of said first and second members.

144. An apparatus as set forth in claim 138 further including a cutter assembly connected with said base and operable to cut the suture at a location disposed between the first and second members.

145. An apparatus for use in securing a suture relative to body tissue, said apparatus comprising a base, a first member connected with said base and connectable with the suture, said first member being urged in a direction toward the body tissue under the influence of tension force transmitted to the first member through the suture, a second member connected with said base and engageable with a retainer which is disposed adjacent to the suture, said second member being effective to transmit force to the retainer urging the retainer toward the body tissue, and a connector assembly which is connected with said base and is operable to connect the retainer to the suture when there is both the transmission of a first predetermined force from the suture to the first member and the transmission of a second predetermined force from the second member to the retainer.

146. An apparatus as set forth in claim 145 wherein said connector assembly includes a vibration applicator member which transmits ultrasonic vibratory energy to the retainer to heat material of the retainer when there is both the transmission of the first predetermined force from the suture to the first member and the transmission of the second predetermined force from the second member to the retainer.

147. An apparatus as set forth in claim 145 wherein said connector assembly includes clamp members and an actuator which presses said clamp members against opposite sides of the retainer to deform material of the retainer.

148. An apparatus as set forth in claim 145 further including a first solid state device to which force is transmitted from said first member and a second solid state device to which force is transmitted from said second member, said first solid state device being effective to provide an output signal which is indicative of the transmission of the first predetermined force from the suture to the first member, said second solid state device being effective to provide an output signal which is indicative of the transmission of the second predetermined force from said second member to the retainer.

149. An apparatus as set forth in claim 145 further including a cutter assembly connected with said base and operable to cut the suture at a location disposed between said first and second members.

150. An apparatus for use in securing first and second sections of a suture relative to body tissue, said apparatus comprising a base, a first member connected with said base and connectable with the first and second sections of the suture, said first member being urged in a direction toward the body tissue under the influence of tension force transmitted through the suture, a second member connected with said base, said second member being urged toward said first member under the influence of force transmitted between said second member and the body tissue, and a connector assembly which is connected with said base and is operable to connect the first and second sections of the suture together when there is both the transmission of a first predetermined force to the first member and the transmission of a second predetermined force between said second member and the body tissue.

151. An apparatus as set forth in claim 150 wherein said connector assembly includes a vibration applicator member which transmits ultrasonic vibratory energy to at least one of the first and second sections of the suture to heat material of the one of the first and second sections of the suture when there is both the transmission of the first predetermined force from the suture to the first member and the transmission of the second predetermined force between the second member and the body tissue.

152. An apparatus as set forth in claim 150 wherein said connector assembly includes clamp members and an actuator which presses said clamp members against the first and second sections of the suture to press the first and second sections of the suture against each other.

153. An apparatus as set forth in claim 152 wherein at least one of said clamp members is effective to apply ultrasonic vibratory energy to at least one of the sections of the suture.

154. An apparatus as set forth in claim 150 further including a first solid state device to which force is transmitted from said first member and a second solid state device to which force is transmitted from said second member, said first solid state device being effective to provide an output signal which is indicative of the transmission of the first predetermined force from the first and second sections of the suture to the first member, said second solid state device being effective to provide an output signal which is indicative of the transmission of the second predetermined force between said second member and the body tissue.

155. An apparatus as set forth in claim 150 further including a cutter assembly connected with said base and operable to cut the first and second sections of the suture at a location between said first and second members.

156. An apparatus for use in securing a suture relative to a bone in a patient's body, said apparatus comprising an anchor formed of a single piece of bone, said anchor including a cylindrical body portion having a longitudinal central axis and a pointed end portion having a central axis which is coincident with the longitudinal central axis of said body portion, said body portion including first and second openings which extend through said body portion in a direction transverse to the longitudinal central axis of said body portion and which receive the suture, said second opening having a central axis which extends parallel to a central axis of said first opening and said pointed end portion having surface means for forming an opening in the bone in the patient's body under the influence of force applied against a trailing end of said body portion in a direction extending along the longitudinal central axis of said body portion.

157. An apparatus as set forth in claim 156 wherein a first portion of said second opening is formed in said body portion of said anchor and a second portion of said second opening is formed in said pointed end portion of said anchor.

158. An apparatus as set forth in claim 156 wherein said anchor is formed of a single piece of freeze dried bone.

159. An apparatus as set forth in claim 156 wherein the bone is allogenic bone.

160. An apparatus as set forth in claim 156 wherein the bone is autogenic bone.

161. An apparatus as set forth in claim 156 wherein the bone is xenogenic bone.

162. An apparatus as set forth in claim 156 wherein the bone is cortical bone.

* * * * *